(12) United States Patent
von Hoffmann et al.

(10) Patent No.: US 10,111,695 B2
(45) Date of Patent: *Oct. 30, 2018

(54) DISTAL BONE ANCHORS FOR BONE FIXATION WITH SECONDARY COMPRESSION

(71) Applicant: DePuy Synthes Products, Inc., Raynham, MA (US)

(72) Inventors: Gerard von Hoffmann, Coto de Caza, CA (US); Victor V. Cachia, San Juan Capistrano, CA (US); Brad S. Culbert, Rancho Santa Margarita, CA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/023,192

(22) Filed: Sep. 10, 2013

(65) Prior Publication Data

US 2014/0142629 A1    May 22, 2014

Related U.S. Application Data

(63) Continuation of application No. 13/466,350, filed on May 8, 2012, now Pat. No. 8,551,094, which is a (Continued)

(51) Int. Cl.
*A61B 17/74* (2006.01)
*A61B 17/86* (2006.01)
*A61B 17/68* (2006.01)

(52) U.S. Cl.
CPC .......... *A61B 17/8625* (2013.01); *A61B 17/68* (2013.01); *A61B 17/742* (2013.01);
(Continued)

(58) Field of Classification Search
CPC ............ A61B 17/8695; A61B 17/8685; A61B 2017/8655; A61B 17/748; A61B 17/746; A61B 17/742; A61B 17/74
(Continued)

(56) References Cited

U.S. PATENT DOCUMENTS 1,802,560 A    4/1931  Kerwin
2,077,804 A    4/1937  Morrison
(Continued)

FOREIGN PATENT DOCUMENTS

AU    2003261286    2/2010
CN     1177918 A    4/1998
(Continued)

OTHER PUBLICATIONS

Communication pursuant to Article 96(2) EPC, dated Apr. 19, 2007 in related European Application No. 02719402.6, 3 pages.
(Continued)

*Primary Examiner* — Julianna N Harvey
(74) *Attorney, Agent, or Firm* — Baker & Hostetler LLP

(57) ABSTRACT

Disclosed is a bone fracture fixation device, such as for reducing and compressing fractures in the proximal femur. The fixation device includes an elongate body with a helical cancellous bone anchor on a distal end. An axially moveable proximal anchor is carried by the proximal end of the fixation device. The device is rotated into position across the fracture or separation between adjacent bones and into the adjacent bone or bone fragment, and the proximal anchor is distally advanced to apply secondary compression and lock the device into place. The device may also be used for soft tissue attachments.

20 Claims, 17 Drawing Sheets

Related U.S. Application Data continuation of application No. 11/050,975, filed on Feb. 4, 2005, now abandoned, which is a continuation of application No. 10/012,687, filed on Nov. 13, 2001, now Pat. No. 6,908,465, which is a continuation-in-part of application No. 09/822,803, filed on Mar. 30, 2001, now Pat. No. 6,511,481.

(52) U.S. Cl.
CPC .......... *A61B 17/744* (2013.01); *A61B 17/746* (2013.01); *A61B 17/869* (2013.01); *A61B 17/8685* (2013.01)

(58) Field of Classification Search
USPC ........ 606/258–259, 62–63, 65–68, 286–289, 606/304, 306, 319–320
See application file for complete search history.

(56) References Cited

U.S. PATENT DOCUMENTS

| | | |
|---|---|---|
| 2,121,193 A | 6/1938 | Hanicke |
| 2,388,056 A | 10/1945 | Hendricks |
| 2,485,531 A | 10/1949 | Dzus et al. |
| 2,489,870 A | 10/1949 | Dzus |
| 2,570,465 A | 10/1951 | Lundholm |
| 3,115,804 A | 12/1963 | Johnson |
| 3,489,143 A | 1/1970 | Holloran |
| 3,842,825 A | 10/1974 | Wagner |
| 4,052,988 A | 10/1977 | Doddi et al. |
| 4,175,555 A | 11/1979 | Herbert |
| 4,262,665 A | 4/1981 | Roalstad et al. |
| 4,275,717 A | 9/1981 | Bolesky |
| 4,341,206 A | 7/1982 | Perrett et al. |
| 4,456,005 A | 6/1984 | Lichty |
| 4,463,753 A | 8/1984 | Gustilo |
| 4,488,543 A | 12/1984 | Tornier |
| 4,532,660 A | 8/1985 | Field |
| 4,537,185 A | 8/1985 | Stednitz |
| 2,173,655 A | 10/1986 | Himoud |
| 4,632,101 A | 12/1986 | Freedland |
| 4,640,271 A | 2/1987 | Lower |
| 4,641,640 A | 2/1987 | Griggs |
| 4,646,741 A | 3/1987 | Smith |
| 4,667,663 A | 5/1987 | Miyata |
| 4,688,561 A | 8/1987 | Reese |
| 4,721,103 A | 1/1988 | Freedland |
| 4,743,257 A | 5/1988 | Tormala |
| 4,760,843 A | 8/1988 | Fischer et al. |
| 4,790,304 A | 12/1988 | Rosenberg |
| 4,796,612 A | 1/1989 | Reese |
| 4,873,976 A | 1/1989 | Schreiber |
| 4,815,909 A | 3/1989 | Simons |
| 4,827,917 A | 5/1989 | Brunfield |
| 4,858,601 A | 8/1989 | Glisson |
| 4,889,119 A | 12/1989 | Jamiolkowski et al. |
| 4,898,186 A | 2/1990 | Ikada et al. |
| 4,903,692 A | 2/1990 | Reese |
| 4,917,554 A | 4/1990 | Bronn |
| 4,927,421 A | 5/1990 | Goble et al. |
| 4,940,467 A | 7/1990 | Tronzo |
| 4,959,064 A | 9/1990 | Engelhardt |
| 4,963,144 A | 10/1990 | Huene |
| 4,968,317 A | 11/1990 | Tormala |
| 4,978,349 A | 12/1990 | Frigg |
| 4,988,351 A | 1/1991 | Paulos et al. |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,167,663 A | 12/1992 | Brumfield |
| 5,167,664 A * | 12/1992 | Hodorek ............ A61B 17/8685 606/306 |
| 5,217,462 A | 6/1993 | Asnis et al. |
| 5,234,431 A | 8/1993 | Keller |
| 5,242,447 A | 9/1993 | Borzone |
| 5,246,441 A | 9/1993 | Ross et al. |
| 5,250,049 A | 10/1993 | Michael |
| 5,300,074 A | 4/1994 | Frigg |
| 5,312,410 A | 5/1994 | Miller et al. |
| 5,334,184 A | 8/1994 | Bimman |
| 5,334,204 A | 8/1994 | Clewett et al. |
| 5,364,398 A | 11/1994 | Chapman et al. |
| 5,370,646 A | 12/1994 | Reese et al. |
| 5,370,661 A | 12/1994 | Branch |
| 5,382,248 A | 1/1995 | Jacobson et al. |
| 5,387,213 A | 2/1995 | Breard |
| 5,415,661 A | 5/1995 | Holmes |
| 5,449,359 A | 9/1995 | Groiso |
| 5,449,361 A | 9/1995 | Preissmann |
| 5,452,748 A | 9/1995 | Simmons et al. |
| 5,464,427 A | 11/1995 | Curtis et al. |
| 5,470,333 A | 11/1995 | Ray |
| 5,496,318 A | 3/1996 | Howland et al. |
| 5,498,265 A | 3/1996 | Asnis et al. |
| 5,501,695 A | 3/1996 | Anspach, Jr. et al. |
| 5,520,690 A | 5/1996 | Errico et al. |
| 5,527,312 A | 6/1996 | Ray |
| 5,536,127 A | 7/1996 | Pennig |
| 5,540,688 A | 7/1996 | Navas |
| 5,545,164 A | 8/1996 | Howland |
| 5,549,610 A | 8/1996 | Russell et al. |
| 5,558,674 A | 9/1996 | Heggeness et al. |
| D374,287 S | 10/1996 | Goble et al. |
| 5,569,248 A | 10/1996 | Mathews |
| 5,569,251 A | 10/1996 | Baker et al. |
| 5,569,548 A | 10/1996 | Koike et al. |
| 5,591,168 A | 1/1997 | Judet et al. |
| 5,609,634 A | 3/1997 | Voydeville |
| 5,618,142 A | 4/1997 | Sonden et al. |
| 5,618,314 A | 4/1997 | Harwin et al. |
| 5,626,613 A | 5/1997 | Schmieding |
| 5,628,751 A | 5/1997 | Sander et al. |
| 5,643,320 A | 7/1997 | Lower et al. |
| 5,645,599 A | 7/1997 | Samani |
| 5,649,931 A | 7/1997 | Bryant et al. |
| 5,662,683 A | 9/1997 | Kay |
| 5,667,508 A | 9/1997 | Errico et al. |
| 5,669,915 A | 9/1997 | Caspar et al. |
| 5,713,903 A * | 2/1998 | Sander ................. A61L 31/148 606/326 |
| 5,720,753 A | 2/1998 | Sander et al. |
| 5,725,541 A | 3/1998 | Anspach, Jr. et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,282 A | 4/1998 | Anspach, III et al. |
| 5,743,914 A | 4/1998 | Skiba |
| 5,772,662 A | 6/1998 | Chapman et al. |
| 5,782,865 A | 7/1998 | Grotz |
| 5,810,821 A | 9/1998 | Vandewalle |
| 5,849,004 A | 12/1998 | Bramlet |
| 5,871,485 A | 2/1999 | Rao et al. |
| 5,893,850 A | 4/1999 | Cachia |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,924 A | 9/1999 | Tormala et al. |

(56) References Cited

U.S. PATENT DOCUMENTS

| | | | |
|---|---|---|---|
| 5,968,044 A | 10/1999 | Nicholson et al. | |
| 5,976,139 A | 11/1999 | Bramlet | |
| 5,984,927 A | 11/1999 | Kiena et al. | |
| 5,984,966 A | 11/1999 | Kiena et al. | |
| 5,989,255 A * | 11/1999 | Pepper et al. | 606/916 |
| 5,993,459 A | 11/1999 | Larsen et al. | |
| 5,997,538 A | 12/1999 | Asnis et al. | |
| 5,997,541 A | 12/1999 | Schenk | |
| 6,001,100 A | 12/1999 | Sherman et al. | |
| 6,001,101 A | 12/1999 | Augagneur et al. | |
| 6,004,327 A | 12/1999 | Asnis et al. | |
| 6,005,161 A | 12/1999 | Brekke et al. | |
| 6,007,566 A | 12/1999 | Wenstorm, Jr. | |
| 6,007,580 A | 12/1999 | Lehto et al. | |
| 6,010,513 A | 1/2000 | Tormala et al. | |
| 6,015,410 A | 1/2000 | Tormala et al. | |
| 6,019,762 A | 2/2000 | Cole | |
| 6,022,352 A | 2/2000 | Vandewalle | |
| 6,030,162 A | 2/2000 | Huebner | |
| 6,068,648 A | 2/2000 | Cole et al. | |
| 6,036,701 A | 3/2000 | Rosenman | |
| 6,048,342 A | 4/2000 | Zucherman et al. | |
| 6,066,142 A | 5/2000 | Serbousek et al. | |
| 6,083,244 A | 7/2000 | Lubbers et al. | |
| 6,102,914 A | 8/2000 | Bulstra et al. | |
| 6,123,711 A * | 9/2000 | Winters | A61B 17/0401 606/304 |
| 6,126,661 A | 10/2000 | Faccioli et al. | |
| 6,126,663 A | 10/2000 | Hair | |
| 6,146,384 A | 11/2000 | Lee et al. | |
| 6,161,350 A | 12/2000 | Espinosa | |
| 6,162,234 A | 12/2000 | Friedland et al. | |
| 6,168,595 B1 | 1/2001 | Durham et al. | |
| 6,168,597 B1 | 1/2001 | Biedermann et al. | |
| 6,183,472 B1 | 2/2001 | Lutz | |
| 6,183,474 B1 | 2/2001 | Bramlet et al. | |
| 6,248,108 B1 | 6/2001 | Tormala et al. | |
| 6,251,111 B1 | 6/2001 | Barker et al. | |
| 6,267,765 B1 | 7/2001 | Taylor et al. | |
| 6,267,767 B1 | 7/2001 | Strobel et al. | |
| 6,287,313 B1 | 9/2001 | Sasso | |
| 6,290,701 B1 | 9/2001 | Enayati | |
| 6,306,136 B1 | 10/2001 | Baccelli | |
| 6,319,254 B1 | 11/2001 | Giet et al. | |
| 6,328,739 B1 * | 12/2001 | Liu | A61B 17/7041 606/264 |
| 6,348,053 B1 | 2/2002 | Cachia | |
| 6,355,043 B1 | 3/2002 | Adam | |
| 6,361,537 B1 | 3/2002 | Anderson | |
| 6,361,538 B1 | 3/2002 | Fenaroli et al. | |
| 6,371,989 B1 | 4/2002 | Chauvin et al. | |
| 6,379,355 B1 | 4/2002 | Zucherman et al. | |
| 6,379,363 B1 | 4/2002 | Herrington et al. | |
| 6,423,061 B1 | 7/2002 | Bryant | |
| 6,423,067 B1 | 7/2002 | Eisermann | |
| 6,440,169 B1 | 8/2002 | Elberg et al. | |
| 6,458,134 B1 | 10/2002 | Songer et al. | |
| 6,468,277 B1 | 10/2002 | Justin et al. | |
| 6,468,309 B1 | 10/2002 | Lieberman | |
| 6,485,491 B1 | 11/2002 | Farris et al. | |
| 6,485,518 B1 | 11/2002 | Cornwall et al. | |
| 6,488,693 B2 | 12/2002 | Gannoe et al. | |
| 6,491,714 B1 | 12/2002 | Bennett | |
| 6,506,192 B1 | 1/2003 | Gertzman et al. | |
| 6,511,481 B2 * | 1/2003 | von Hoffmann | A61B 17/68 606/60 |
| 6,517,543 B1 | 2/2003 | Berrevoets et al. | |
| 6,520,907 B1 | 2/2003 | Foley et al. | |
| 6,527,774 B2 | 3/2003 | Lieberman | |
| 6,540,747 B1 | 4/2003 | Marino | |
| 6,544,265 B2 | 4/2003 | Lieberman | |
| 6,547,793 B1 | 4/2003 | McGuire | |
| 6,547,795 B2 | 4/2003 | Schneidermann | |
| 6,551,319 B2 | 4/2003 | Lieberman | |
| 6,551,322 B1 | 4/2003 | Lieberman | |
| 6,554,831 B1 | 4/2003 | Rivard et al. | |
| 6,558,389 B2 | 5/2003 | Clark et al. | |
| 6,562,046 B2 | 5/2003 | Sasso | |
| 6,579,293 B1 | 6/2003 | Chandran | |
| 6,582,453 B1 | 6/2003 | Tran et al. | |
| 6,585,730 B1 | 7/2003 | Foerster | |
| 6,585,740 B2 | 7/2003 | Schlapfer | |
| 6,589,249 B2 | 7/2003 | Sater et al. | |
| 6,599,297 B1 | 7/2003 | Carlsson et al. | |
| 6,610,091 B1 | 8/2003 | Relley | |
| 6,613,050 B1 | 9/2003 | Wagner et al. | |
| 6,626,944 B1 | 9/2003 | Taylor | |
| 6,632,224 B2 | 10/2003 | Cachia et al. | |
| 6,635,059 B2 | 10/2003 | Randall et al. | |
| 6,648,890 B2 | 11/2003 | Culbert et al. | |
| 6,648,893 B2 | 11/2003 | Dudasik | |
| 6,669,698 B1 | 12/2003 | Tromanhauser et al. | |
| 6,669,729 B2 | 12/2003 | Chin | |
| 6,673,074 B2 | 1/2004 | Shluzas | |
| 6,685,706 B2 | 2/2004 | Padget et al. | |
| 6,692,499 B2 | 2/2004 | Tormalaet et al. | |
| 6,733,534 B2 | 5/2004 | Sherman | |
| 6,752,831 B2 | 6/2004 | Sybert | |
| 6,761,720 B1 | 7/2004 | Senegas | |
| 6,770,075 B2 | 8/2004 | Howland | |
| 6,796,983 B1 | 9/2004 | Zucherman et al. | |
| 6,808,526 B1 | 10/2004 | Magerl et al. | |
| 6,835,205 B2 | 12/2004 | Atkinson et al. | |
| 6,875,215 B2 | 4/2005 | Taras et al. | |
| 6,887,243 B2 | 5/2005 | Culbert | |
| 6,890,333 B2 | 5/2005 | von Hoffmann et al. | |
| 6,908,465 B2 * | 6/2005 | von Hoffmann | A61B 17/68 606/67 |
| 6,916,323 B2 | 6/2005 | Kitchens et al. | |
| 6,921,403 B2 | 6/2005 | Cragg et al. | |
| 6,929,606 B2 | 8/2005 | Ritland | |
| 6,942,668 B2 | 9/2005 | Padget et al. | |
| 6,945,975 B2 | 9/2005 | Dalton | |
| 6,949,100 B1 | 9/2005 | Venturini | |
| 6,951,561 B2 | 10/2005 | Warren et al. | |
| 7,060,068 B2 | 6/2006 | Tromanhauser et al. | |
| 7,063,701 B2 | 6/2006 | Michelson | |
| 7,063,702 B2 | 6/2006 | Michelson | |
| 7,070,601 B2 * | 7/2006 | Culbert | A61B 17/685 606/311 |
| 7,074,203 B1 | 7/2006 | Johanson et al. | |
| 7,094,239 B1 | 8/2006 | Michelson | |
| 7,326,211 B2 | 8/2008 | Padget et al. | |
| 7,556,629 B2 | 7/2009 | von Hoffmann et al. | |
| 7,686,807 B2 | 3/2010 | Padget et al. | |
| 7,846,183 B2 | 12/2010 | Blain | |
| 8,551,094 B2 * | 10/2013 | von Hoffmann | A61B 17/68 606/304 |
| 8,715,014 B2 | 5/2014 | Culbert | |
| 8,715,284 B2 | 5/2014 | Culbert | |
| 9,408,648 B2 | 8/2016 | Culbert | |
| 2001/0027320 A1 | 10/2001 | Sasso | |
| 2001/0049529 A1 | 12/2001 | Cachia et al. | |
| 2002/0055740 A1 | 5/2002 | Lieberman | |
| 2002/0143331 A1 | 10/2002 | Zucherman et al. | |
| 2002/0143335 A1 | 10/2002 | von Hoffmann et al. | |
| 2003/0028250 A1 | 2/2003 | Reiley et al. | |
| 2003/0063582 A1 | 4/2003 | Culbert | |
| 2003/0065330 A1 | 4/2003 | Zucherman et al. | |
| 2003/0220643 A1 | 11/2003 | Ferree | |
| 2003/0229350 A1 | 12/2003 | Kay | |
| 2004/0006391 A1 | 1/2004 | Reiley | |
| 2004/0008949 A1 | 1/2004 | Culbert | |
| 2004/0049190 A1 | 3/2004 | Biedermann et al. | |
| 2004/0097941 A1 | 5/2004 | Weiner et al. | |
| 2004/0127906 A1 | 7/2004 | Culbert et al. | |
| 2004/0143734 A1 | 7/2004 | Buer et al. | |
| 2004/0199162 A1 | 10/2004 | von Hoffmann et al. | |
| 2004/0225292 A1 | 11/2004 | Sasso et al. | |
| 2004/0254575 A1 | 12/2004 | Obenchain et al. | |
| 2005/0033434 A1 | 2/2005 | Berry | |
| 2005/0090833 A1 | 4/2005 | DiPoto | |
| 2005/0119657 A1 | 6/2005 | Goldsmith | |
| 2005/0131411 A1 | 6/2005 | Culbert | |

(56) References Cited

U.S. PATENT DOCUMENTS

| | | |
|---|---|---|
| 2005/0137595 A1 | 6/2005 | von Hoffmann et al. |
| 2005/0143734 A1 | 6/2005 | Culbert et al. |
| 2005/0149030 A1 | 7/2005 | Serhan |
| 2005/0177240 A1 | 8/2005 | Blain |
| 2005/0216026 A1 | 9/2005 | Culbert |
| 2005/0251142 A1 | 11/2005 | von Hoffmann et al. |
| 2005/0283238 A1 | 12/2005 | Reiley |
| 2006/0015105 A1 | 1/2006 | Warren et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0079908 A1 | 4/2006 | Lieberman |
| 2006/0084977 A1 | 4/2006 | Lieberman |
| 2006/0085010 A1 | 4/2006 | Lieberman |
| 2006/0100707 A1 | 5/2006 | Stinson et al. |
| 2006/0122609 A1 | 6/2006 | Mirkovic et al. |
| 2006/0122610 A1 | 6/2006 | Culbert et al. |
| 2006/0195103 A1 | 8/2006 | Padget et al. |
| 2006/0217711 A1 | 9/2006 | Stevens et al. |
| 2007/0016191 A1 | 1/2007 | Culbert et al. |
| 2007/0118132 A1 | 5/2007 | Culbert et al. |
| 2007/0123868 A1 | 5/2007 | Culbert et al. |
| 2008/0097436 A1 | 4/2008 | Culbert et al. |
| 2008/0108996 A1 | 5/2008 | Padget et al. |
| 2008/0306537 A1 | 12/2008 | Culbert et al. |
| 2009/0069813 A1 | 3/2009 | von Hoffmann et al. |

FOREIGN PATENT DOCUMENTS

| | | |
|---|---|---|
| DE | 198 32 798 | 11/1999 |
| DE | 201 01 793 | 5/2001 |
| EP | 0 525 352 A1 | 2/1993 |
| EP | 0 625 336 | 11/1994 |
| EP | 0 853 929 A2 | 7/1998 |
| EP | 1 046 376 A1 | 4/2000 |
| EP | 1 378 205 | 7/2003 |
| EP | 1 757 529 | 2/2007 |
| EP | 2 100 565 | 9/2009 |
| EP | 1 523 278 | 11/2009 |
| FR | 2 699 065 | 12/1992 |
| FR | 2 745 709 | 3/1996 |
| FR | 2 728 778 | 7/1996 |
| FR | 2 800 601 | 11/1999 |
| FR | 2 801 189 | 11/1999 |
| FR | 2 808 182 | 4/2000 |
| GB | 2157788 A | 10/1985 |
| GB | 2173565 A | 10/1986 |
| JP | 64-52439 | 2/1989 |
| JP | 10-85232 A | 3/1989 |
| JP | 11-89854 A | 7/1989 |
| JP | 6-319742 A | 11/1994 |
| JP | 2005-533627 | 11/2005 |
| WO | WO 91/09572 | 12/1989 |
| WO | WO 1999/62417 | 12/1999 |
| WO | WO 00/67652 | 11/2000 |
| WO | WO 2001/80751 | 11/2001 |
| WO | WO 2002/43601 | 6/2002 |
| WO | WO 2002/078555 | 10/2002 |
| WO | WO 03/043488 | 5/2003 |
| WO | WO 04/008949 | 1/2004 |
| WO | WO 04/064603 | 8/2004 |
| WO | WO 04/078220 | 9/2004 |
| WO | WO 04/078221 | 9/2004 |
| WO | WO 04/098453 | 11/2004 |
| WO | WO 06/063083 | 6/2006 |
| WO | WO 2007/048038 | 4/2007 |
| WO | WO 07/124130 | 11/2007 |

OTHER PUBLICATIONS

European Search Report for Application No. 02719402.6 (the European counterpart of the parent application) dated Jun. 22, 2006.

Extended European Search Report received in European Application No. 09152476.9, dated Apr. 3, 2009, 5 pages.

International Search Report for Application No. PCT/US2005/044321 (the PCT counterpart of the parent application) dated Apr. 13, 2006.

King, M.D., Don. "Internal Fixation for Lumbosacral Fusion", The Journal of Bone & Joint Surgery. J Bone Joint Surg Am. 1948;30:560-578.

Notice of Acceptance received in related Australian Appl. No. 2002250488, dated Jun. 18, 2007, 3 pages.

Notice of Allowance received in related Canadian Appl. No. 2,442,334, dated May 25, 2009, 1 page.

Notice of Preliminary Rejection received in related Korean Appl. No. 2003-7012847, dated Apr. 29, 2008, 12 pages.

Office Action received in related Australian Appl. No. 2002250488, dated Sep. 19, 2005, 2 pages.

Office Action received in related Chinese Appl. No. 02810329.7, dated Apr. 6, 2007, 6 pages.

Office Action received in U.S. Appl. No. 10/623,193; dated Jul. 22, 2009, 6 pages.

Official Report received in related Canadian Appl. No. 2,442,334, dated Jul. 3, 2008, 2 pages.

Apr. 22, 2004 International Search Report for App. No. PCT/US03/23645 filed Jul. 18, 2003.

Apr. 19, 2007 Office Action for European Application No. 02 719 402.6 filed Mar. 29, 2002.

European Exam Report, re EPO Application No. 09 152 476.9, dated Mar. 12, 2015.

U.S. Appl. No. 09/558,057, filed Apr. 26, 2000 entitled "Bone fixation system".

\* cited by examiner

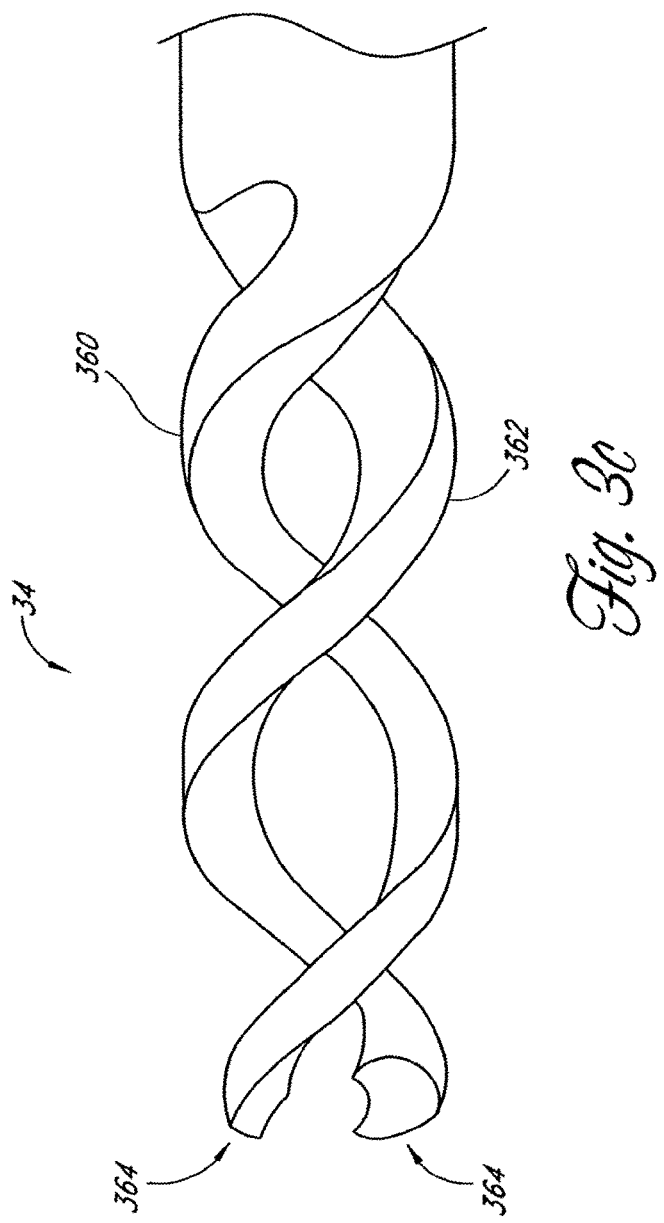

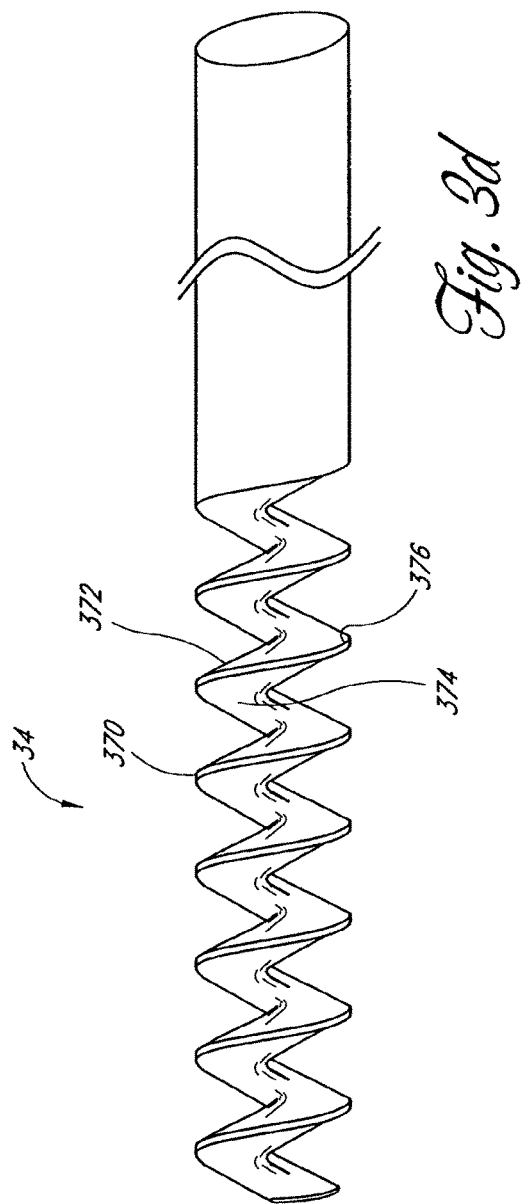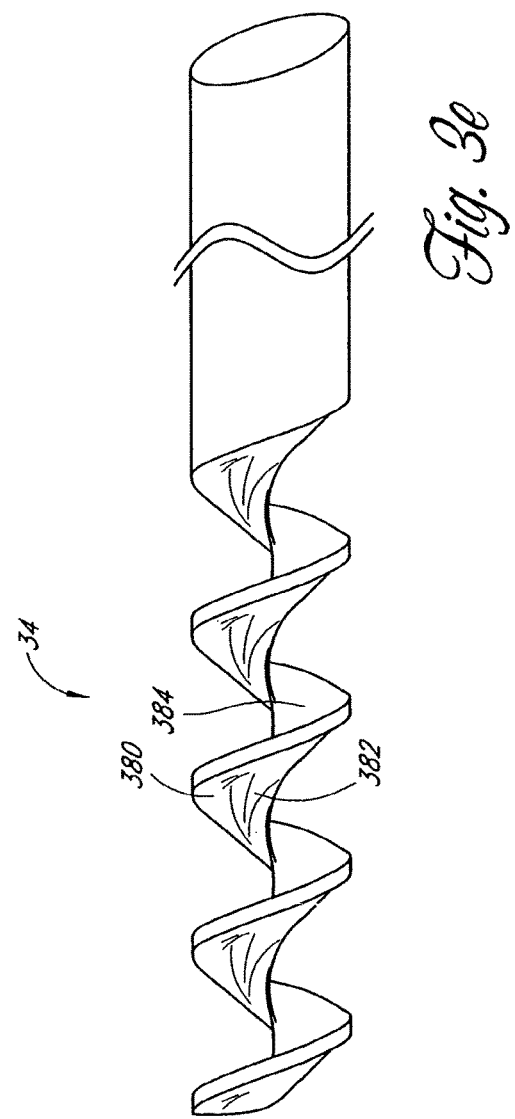

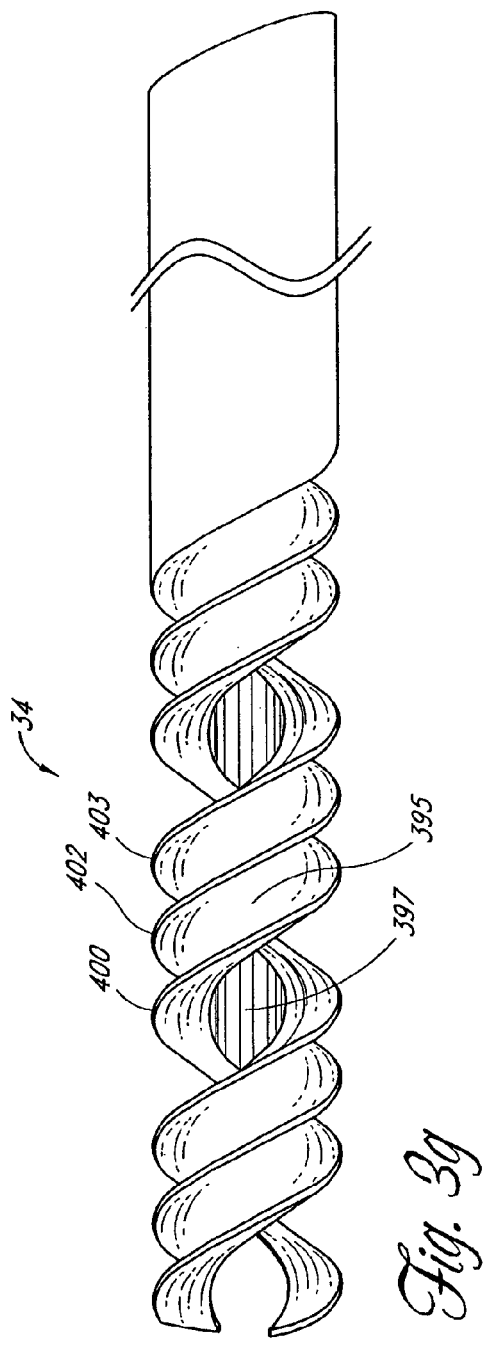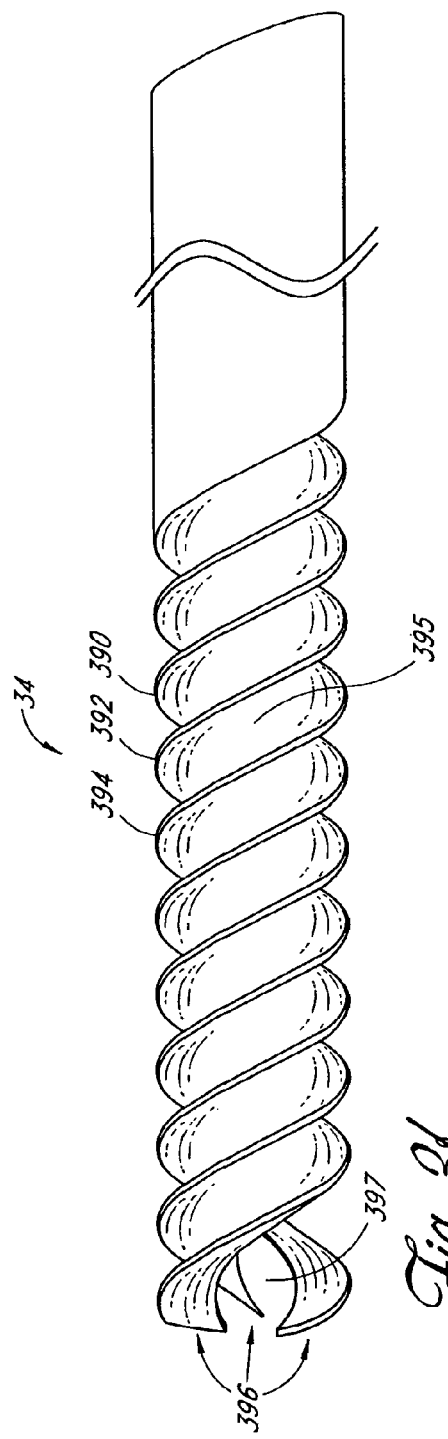

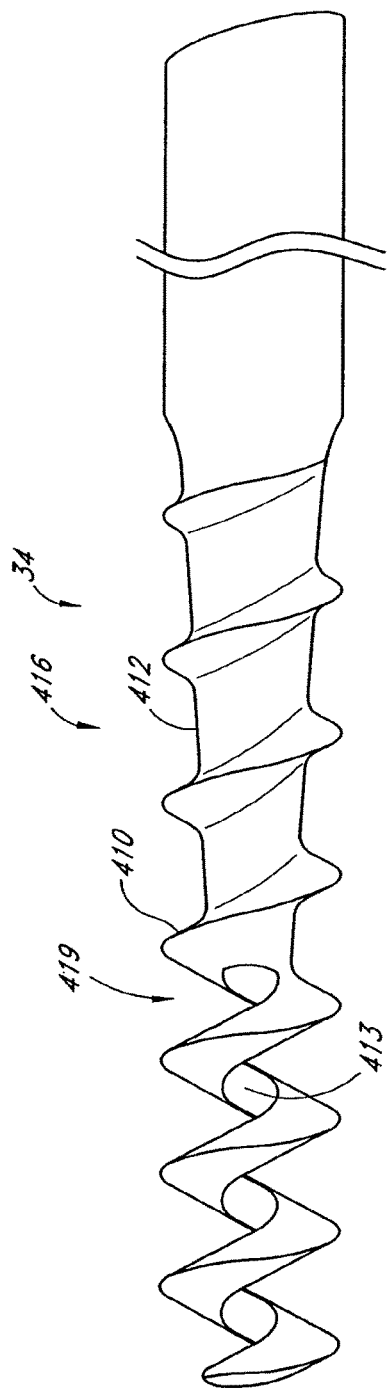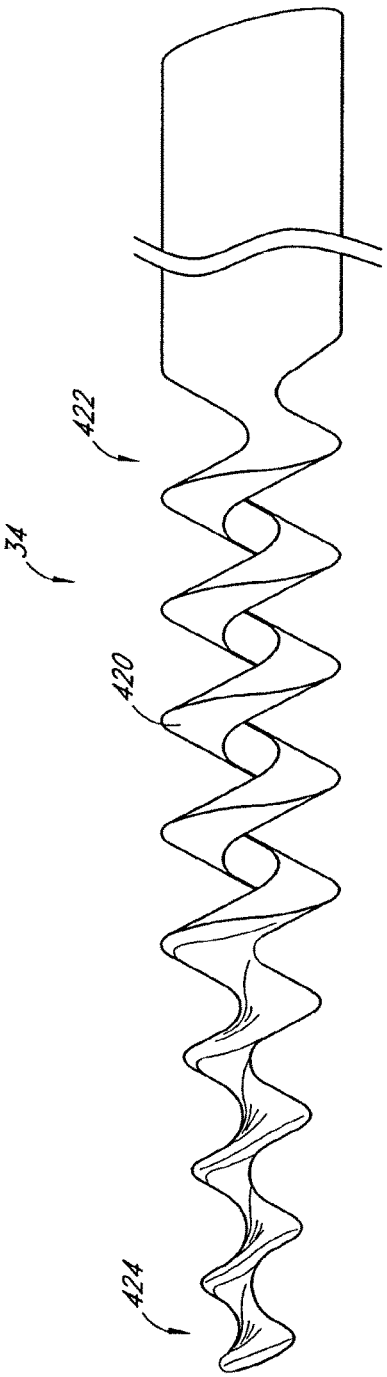
Fig. 3h
Fig. 3i

DISTAL BONE ANCHORS FOR BONE FIXATION WITH SECONDARY COMPRESSION

CROSS-REFERENCE TO RELATED APPLICATIONS

This invention is a continuation of U.S. patent application Ser. No. 13/466,350, filed May 8, 2012, which is a continuation of U.S. patent application Ser. No. 11/050,975, filed Feb. 4, 2005, now abandoned, which is a continuation of U.S. patent application Ser. No. 10/012,687, filed Nov. 13, 2001, now U.S. Pat. No. 6,908,465 issued on Jun. 21, 2005, which is a continuation-in-part of U.S. patent application Ser. No. 09/822,803, filed Mar. 30, 2001, now U.S. Pat. No. 6,511,481 issued on Jan. 28, 2003, the disclosures of which are incorporated by reference herein in their entireties.

TECHNICAL FIELD

The present invention relates to internal bone fracture fixation devices. In one application, the present invention relates to bone fracture fixation devices and methods adapted for fixation, among other fractures, of femoral neck and other proximal femoral fractures.

BACKGROUND

The femur, otherwise known as the thigh bone, generally comprises an elongate shaft extending from the hip to the knee. The proximal end of the shaft includes a head, a neck, a greater trochanter and a lesser trochanter. The head of the femur fits into the acetabular cup of the hip bone to form a ball and socket joint at the hip. The distal end of the femur includes a medial condyle and a lateral condyle. The condyles engage an upper end of the tibia to form the knee joint. Overall, the femur is the longest and strongest bone in the skeleton. However, portions of the femur are extremely susceptible to fracturing.

Pertrochanteric fractures among geriatric patients are the most frequent in connection with those of the region of the neck of the bone. The advanced age and the pathologies which are encountered in these patients make a timely stabilization of skeletal injuries necessary in order to reduce to a minimum the bed confinement and the rehabilitation times. Preferably, devices and procedures are utilized which minimize complications brought about by the so-called immobilization syndrome, which may be lethal for patients in delicate metabolical circumstances. It is also preferable to reduce to a minimum blood losses related to surgical intervention. At the same time, the syntheses means utilized must be stable in order to allow the patient to very timely assume a seated position and, two or three days following the intervention, to reassume an erect posture with progressive bearing of weight.

Internal fixation of femoral fractures in general is one of the most common orthopedic surgical procedures. Fractures of the femur occur in both the proximal portion of the femur and the distal portion of the femur. Fractures of the proximal portion of the femur (hip fractures) are generally classified as femoral neck fractures (capital or sub-capital), intertrochanteric fractures and subtrochanteric fractures. Fractures of the distal portion of the femur (knee fractures) are referred to as supracondylar fractures. Supracondylar fractures generally extend vertically between the condyles at the lower end of the femur to separate the distal portion of the femur into two main bone fragments. A fracture line may be further comminuted to create a plurality of smaller bone fragments. Fractures of the femur which extend into the neck of the bone are generally more difficult to treat than fractures restricted to the shaft of the femur.

Operative treatment of the fractures requires that the fractures be internally fixed and possibly compressed. Fractures of the neck, head or trochanters of the femur have been treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted.

A variety of elongated implants (nail, screw, pin, etc.) have been developed, which are adapted to be positioned along the longitudinal axis of the femoral neck with a leading (distal) end portion in the femoral head so as to stabilize a fracture of the femoral neck. The elongated implant may be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint weight bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by overtightening during the implantation procedure or during post operative loading by the patient's weight.

Thus, notwithstanding the variety of efforts in the prior art, there remains a need for an orthopedic fixation device with improved locking force such as within the femoral head in a femoral neck application, which resists migration and rotation, and which can be easily and rapidly deployed within the bone.

SUMMARY OF THE INVENTION

There is provided in accordance with one aspect of the present invention, a method of securing a first bone fragment to a second bone fragment. The method comprises the steps of drilling a bore through the first bone fragment in the direction of the second bone fragment, and advancing through the bore a fixation device comprising a first portion and a second portion that are coupled to each other. A distal anchor of the fixation device is rotated to secure the fixation device to the second fragment, and the proximal anchor is axially advanced to engage the first fragment and provide compression across the fracture.

In one application of the method, the second bone fragment comprises the head of a femur. Alternatively, the second bone fragment comprises a tibia, a fibula, a femur, a humerus, a radius, or an ulna. The first bone fragment may comprise a condyle.

The method may additionally comprise the step of uncoupling the first portion from the second portion.

In accordance with another aspect of the present invention, there is provided a femoral neck fracture fixation device. The device comprises an elongate body, having a proximal end and a distal end and a helical anchor on the distal end. The helical anchor is wrapped about a central core or axial lumen. An outer edge of the helical anchor defines an outer boundary and the central core or axial lumen defines a minor diameter. A first retention structure is provided on the body, proximal to the anchor. A proximal anchor is moveably carried by the body. The proximal anchor is movable in the distal direction with respect to the body and the retention structure resists proximal movement of the proximal anchor with respect to the body.

In accordance with a further aspect of the present invention, there is provided a bone fracture fixation device. The device comprises an elongate body having a proximal end and a distal end. A cancellous bone anchor is on the distal end. The cancellous bone anchor comprises a helical flange wrapped about a central core or axial lumen. An outer edge of the helical anchor defines an outer boundary and the central core or axial lumen defines a minor diameter. A proximal anchor is axially movably carried on the body. Complimentary surface structures are provided between the body and the proximal anchor that permit advancing the proximal anchor in the distal direction to provide compression across a fracture but that resist axial proximal movement of the proximal anchor.

In accordance with another aspect of the present invention, there is provided a method of treating a femoral fracture. The method comprises the steps of drilling at least one and preferably two or three bores distally into the femur in the direction of a fracture, and advancing into each bore a fixation device that comprises a body having a first portion that forms a distal bone anchor and a second portion that forms a proximal end. A proximal component is rotated to engage the distal anchor with the bone distal to the fracture, and a proximal anchor is advanced distally along the fixation device to compress the fracture.

In accordance with another aspect of the invention a bone fracture fixation device comprises an elongate body having a proximal end and a distal end. The body also includes a helical anchor on the distal end. A first retention structure is on the body located proximal to the anchor. A proximal anchor is moveably carried by the body and has a tubular housing. The tubular housing has at least one barb extending radially outwardly from the tubular housing and defining an engagement surface that lies within a plane that is transverse to a longitudinal axis of the tubular housing. The proximal anchor is movable in the distal direction with respect to the body and the retention structure resists proximal movement of the proximal anchor with respect to the body.

Preferably, the drilling step comprises drilling the bore along an axis which extends into the femoral neck and in the direction of the head of the femur. In one embodiment, the advancing a proximal anchor step comprises axially advancing the proximal anchor without rotating the proximal anchor with respect to the fixation device. The femoral fracture may be a femoral neck fracture (e.g., capital or subcapital), an intertrochanteric fracture or a subtrochanteric fracture.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3C is a side elevational view of a double helix distal anchor.

FIG. 3D is a side elevational view of a "V" thread distal anchor.

FIG. 3E is a side elevational view of a buttress thread distal anchor

FIG. 3F is a side elevational view of a triple helix distal anchor.

FIG. 3G is a side elevational view of a split triple helix distal anchor.

FIG. 3H is a side elevational view of a tapered transition thread distal anchor.

FIG. 3I is a side elevational view of a tapered thread distal anchor.

DETAILED DESCRIPTION

Figure 1:
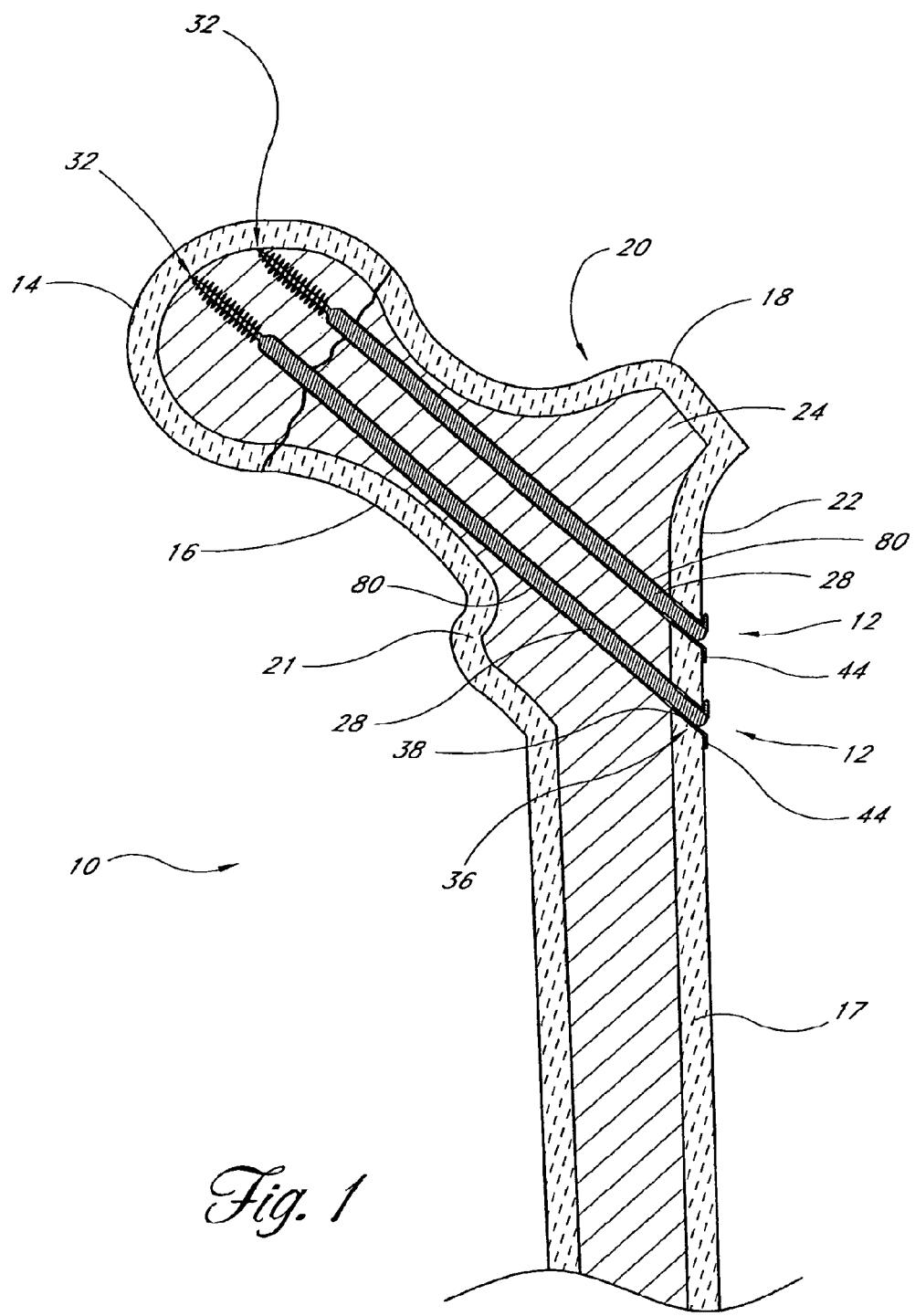
FIG. 1 is a posterior elevational posterior cross section through the proximal portion of the femur, having two femoral neck fracture fixation devices positioned therein.

Although the fixation devices of the present invention will be disclosed primarily in the context of fractures of the proximal femur, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer(s), all of which can be either permanent, absorbable, or combinations.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. Fractures and osteotomies of the mid and hind foot, tarsal arthrodesis and osteotomy, or others as are known to those with skill in the art. One example is the fixation of the medial malleolar avulsion fragment fixation.

The fixation device of the present invention may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, or the pin and or collar may be modified to accept a suture or other material for facilitation of this attachment.

Specific examples include attachment of the posterior tibial tendon to the navicular bone in the Kidner operation. This application may be accomplished using an appropriately sized implant of the present invention along with a washer with distally extending soft tissue spikes. Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion or detachment, such as in the ankle, shoulder or knee can also be accomplished using the devices disclosed herein.

The fixation devices can also be used to aid bone fusion between adjacent bones, bone fragments or any of a variety of articulating joints, such as, for example, a first and a second adjacent vertebral bodies of the spine.

The fixation devices may be used in combination with semi tubular, one-third tubular and dynamic compression plates, both of metallic and absorbable composition, if the collar is modified to match the opening on the plate.

The cannulated design disclosed below can be fashioned to accept an antibiotic impregnated rod for the slow adsorption of medication locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types. The kit may include additional components such as sterilization or disinfectant materials, a skin stapler, bandages, gloves, and basic tools for emergent wound and fracture treatment. Antibiotic rods may be included for wound prophylaxis during transport.

Referring to FIG. 1, there is illustrated a posterior side elevational view of the proximal portion of a femur 10, having a two fixation devices 12 positioned therein. The proximal end of the femur 10 comprises a head 14 connected by way of a neck 16 to the long body or shaft 17 of the femur 10. As illustrated in FIG. 1, the neck 16 is smaller in diameter than the head 14. The neck 16 and head 14 also lie on an axis which, on average in humans, crosses the longitudinal axis of the body 17 of the femur 10 at an angle of about 126°. The risk of fracture at the neck 16 is thus elevated, among other things, by the angular departure of the neck 16 from the longitudinal axis of the body 17 of femur 10 and also the reduced diameter of the neck 16 with respect to the head 14.

The greater trochanter 18 extends outwardly above the junction of the neck 16 and the body 17 of the femur 10. On the medial side of the greater trochanter 18 is the trochanteric fossa 20. This depression accommodates the insertion of the obturator externus muscle. The lesser trochanter 21 is located posteromedially at the junction of the neck 16 and the body 17 of the femur 10. Both the greater trochanter 18 and the lesser trochanter 21 serve for the attachment of muscles. On the posterior surface of the femur 10 at about the same axial level as the lesser trochanter 21 is the gluteal tuberosity 22, for the insertion of the gluteus maximus muscle. Additional details of the femur are well understood in the art and not discussed in further detail herein.

FIG. 1 illustrates a subcapital femoral neck fracture 24. Fractures of the proximal portion of the femur 10 are generally classified as capital or subcapital femoral neck fractures, intertrochanteric fractures and subtrochanteric fractures. All of these fractures will be deemed femoral neck fractures for the purpose of describing the present invention.

Referring to FIGS. 1-4, the fixation device 12 comprises a body 28 extending between a proximal end 30 and a distal end 32. The length, diameter and construction materials of the body 28 can be varied, depending upon the intended clinical application. In embodiments optimized for various fractures in an adult human population, the body 28 will generally be within the range of from about 6 mm to about 150 mm in length after sizing, and within the range of from about 2 mm to about 12 mm in maximum diameter. The major diameter of the helical anchor, discussed below, may be within the range of from about 2.0 mm to about 15 mm. In general, the appropriate dimensions of the body 28 will vary, depending upon the specific fracture. In rough terms, for a malleolar fracture, shaft diameters in the range of from about 3 mm to about 4.5 mm may be used, and lengths within the range of from about 20 mm to about 70 mm. For condylar fractures, shaft diameters within the range of from about 3.5 mm to about 8.0 mm may be used with lengths within the range of from about 25 mm to about 70 mm. For colles fractures (distal radius and ulna), diameters within the range of from about 2.0 mm to about 4.5 mm may be used with any of a variety of lengths within the range of from about 6 mm to about 70 mm.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. Additional details of the distal bone anchor are described below. In general, in a femoral neck application, distal bone anchor 34 is adapted to be rotationally inserted into the cancellous bone within the head 14 of the femur 10, to retain the fixation device 12 within the femoral head.

The proximal end 30 of the fixation device is provided with a proximal anchor 36. Proximal anchor 36 is axially distally moveable along the body 28, to permit compression of the fracture 24 as will be apparent from FIG. 1 and the description below. As will be explained below, complementary locking structures such as threads or ratchet like structures between the proximal anchor 36 and the body 28 resist proximal movement of the anchor 36 with respect to the body 28 under normal use conditions. The proximal anchor 36 can be axially advanced along the body 28 either with or without rotation, depending upon the complementary locking structures as will be apparent from the disclosure herein.

In the illustrated embodiment, proximal anchor 36 comprises a housing 38 such as a tubular body, for coaxial movement along the body 28. The housing 38 is provided with one or more surface structures 40 such as radially inwardly projecting teeth or flanges, for cooperating with complementary surface structures 42 on the body 28. The surface structures 40 and complementary surface structures 42 permit distal axial travel of the proximal anchor 36 with respect to the body 28, but resist proximal travel of the proximal anchor 36 with respect to the body 28. Any of a variety of complementary surface structures which permit one way ratchet like movement may be utilized, such as a plurality of annular rings or helical threads, ramped ratchet structures and the like for cooperating with an opposing ramped structure or pawl.

Retention structures 42 are spaced axially apart along the body 28, between a proximal limit 54 and a distal limit 56. The axial distance between proximal limit 54 and distal limit 56 is related to the desired axial working range of travel of the proximal anchor 36, and thus the range of functional sizes of the fixation device 12. In one embodiment of the fixation device 12, the retention structure 42 comprise a plurality of threads, adapted to cooperate with the retention structures 40 on the proximal anchor 36, which may be a complementary plurality of threads. In this embodiment, the proximal anchor 36 may be distally advanced along the body 28 by rotation of the proximal anchor 36 with respect to the body 28. Proximal anchor 36 may be advantageously removed from the body 28 by reverse rotation, such as to permit removal of the body 28 from the patient. In this embodiment, a flange 44 is preferably provided with a gripping structure to permit a removal tool to rotate the flange 44 with respect to the body 28. Any of a variety of gripping structures may be provided, such as one or more slots, flats, bores or the like. In one embodiment, the flange 44 is provided with a polygonal, and, in particular, a pentagonal or hexagonal circumference. See, e.g. FIG. 4A.

Figure 4A:
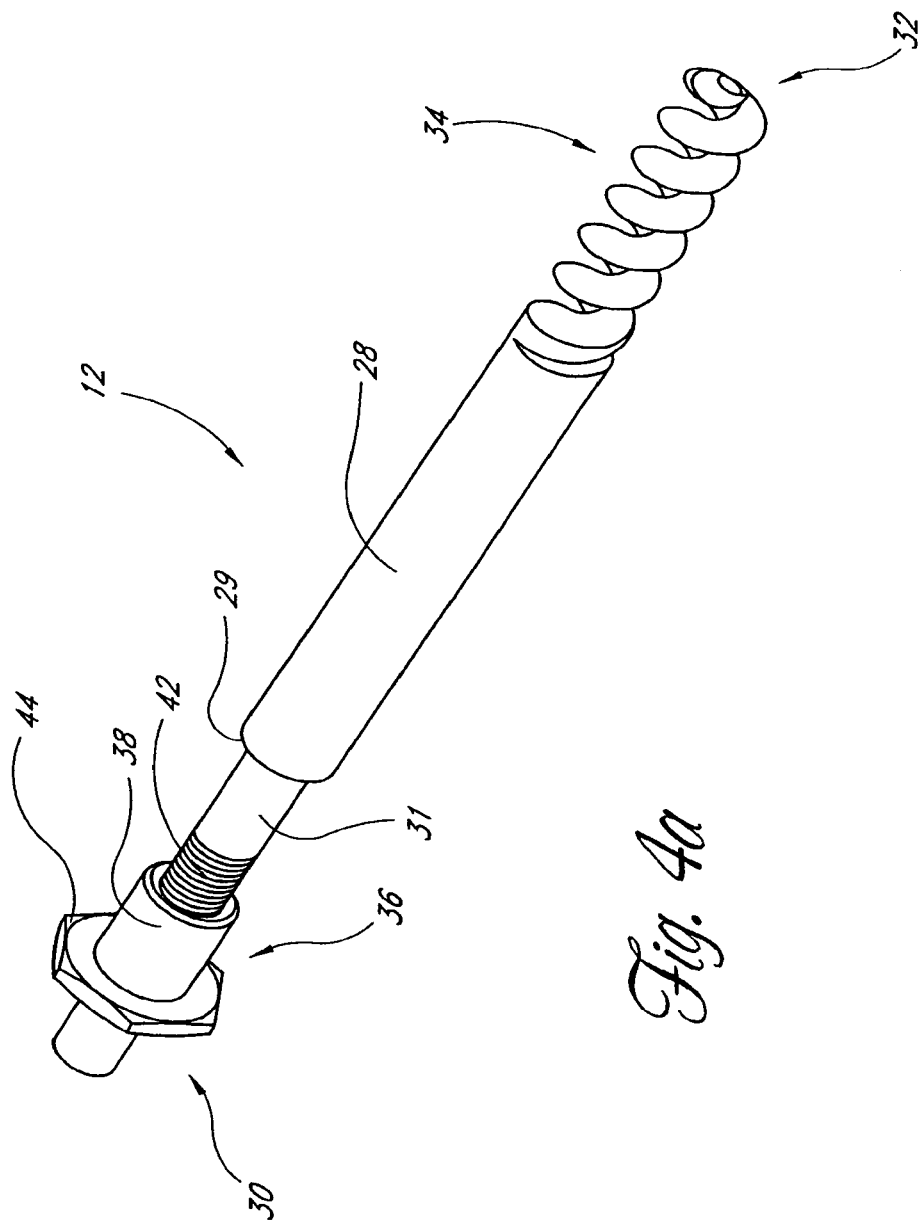
FIG. 4A is a front elevational perspective view of a modified fixation device of the present invention.
Figure 4B:
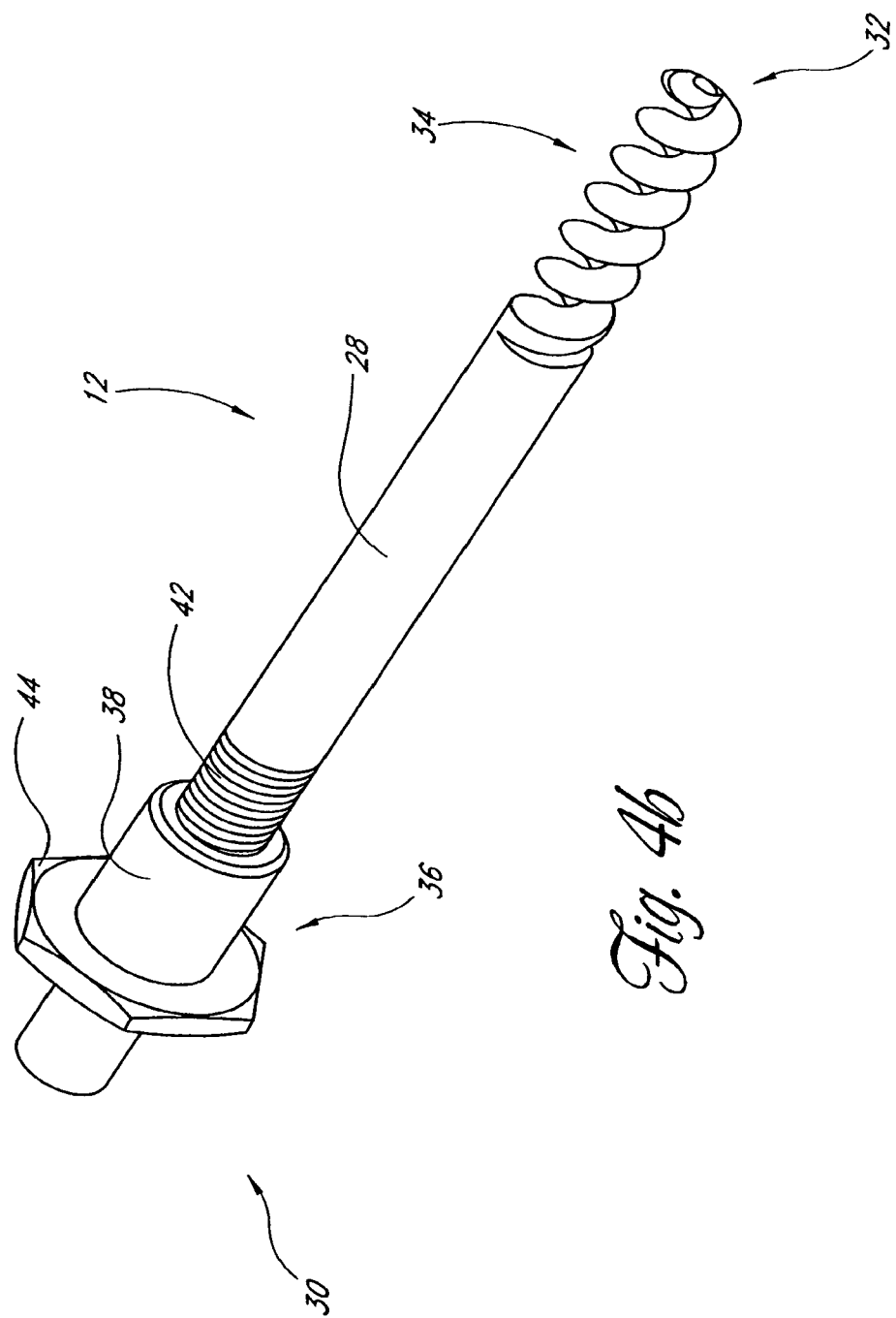
FIG. 4B is a front elevational perspective view of a further modification to the fixation device of the present invention.

FIGS. 4A and 4B additionally illustrate a profile modification that can be made on any of the embodiments discussed herein. Referring to FIG. 4A, the retention structures 42 are positioned on a reduced diameter segment 31. The reduced diameter segment 31 is separated from the remainder of the body 28 by an annular shoulder 29. This construction allows the outside diameter of the tubular housing 38 to be approximately the same as the outside diameter of the distal portion of body 28. In this manner, a single diameter bore hole may be formed in the proximal bone segment, to receive both the body 28 and tubular housing 38 with minimal extra tolerance. Alternatively, as illustrated in FIG. 4B, the body 28 may have the same diameter throughout its axial length with the retention structures 42 formed thereon. In this embodiment, the outside diameter of proximal housing 38 will be larger than the outside diameter throughout the body 28.

Thus, the present invention provides a bone fixation device which can provide compression across a fracture throughout a range of motion following the placement of the distal anchor. The distal anchor may be positioned within the cancellous and/or distal cortical bone, and the proximal anchor may be distally advanced throughout a range to provide compression across the fracture without needing to relocate the distal anchor and without needing to initially locate the distal anchor in a precise position with respect to the proximal side of the bone. Providing a working range throughout which tensioning of the proximal anchor is independent from setting the distal anchor allows a single device to be useful for a wide variety of fractures, as well as eliminates the need for accurate device measurement and accurate placement of the distal anchor. In many applications, the working range is at least about 10% of the overall length of the device, and may be as much as 20% or 30% or more of the overall device length. In the context of a femoral application, working ranges of up to about 10 mm may be provided, since estimates within that range can normally be readily accomplished within the clinical setting. In other applications, such as a metatarsal fracture, a working range in the area of from about 1 mm to about 2 mm may be all that is necessary. The embodiments disclosed herein can be scaled to have a greater or a lesser working range, as will be apparent to those of skill in the art in view of the disclosure herein.

The proximal anchor 36 includes a flange 44 that seats against the outer surface of the femur or tissue adjacent the femur. The flange 44 is preferably an annular flange, to optimize the footprint or contact surface area between the flange 44 and the femur. Circular or polygonal shaped flanges for use in femoral head fixation will generally have a diameter of at least about 4 mm greater than the adjacent body 28 and often within the range of from about 4 mm to about 20 mm or more greater than the adjacent body 28. In a modified embodiment, the flange 44 can be curved to match the curved shape of the femur and further optimize the footprint or contact surface area between the flange 44 and the femur.

Figure 3A:
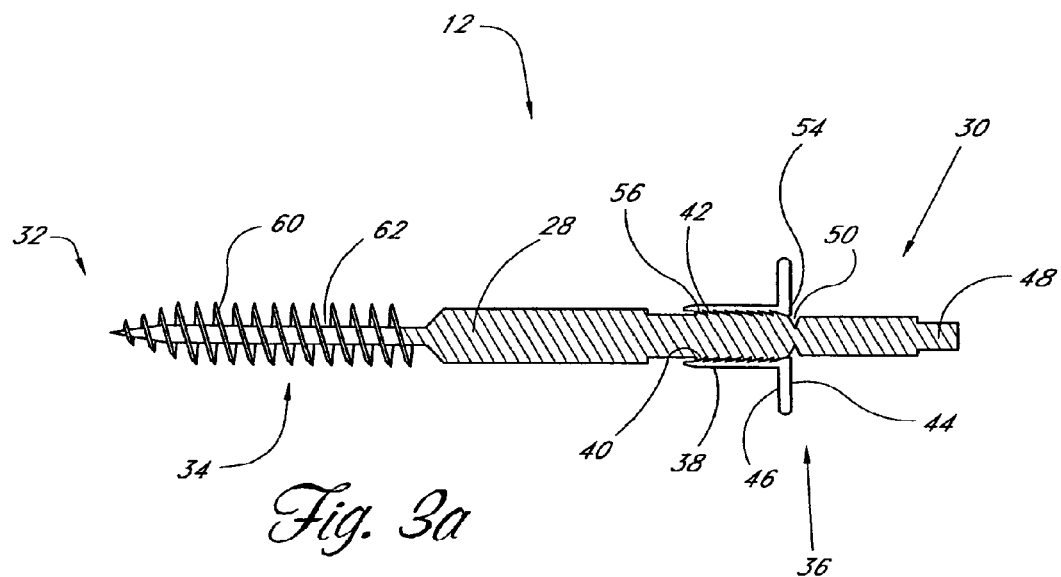
FIG. 3A is a side elevational cross section of a fixation device similar to that of FIG. 1.
Figure 3B:
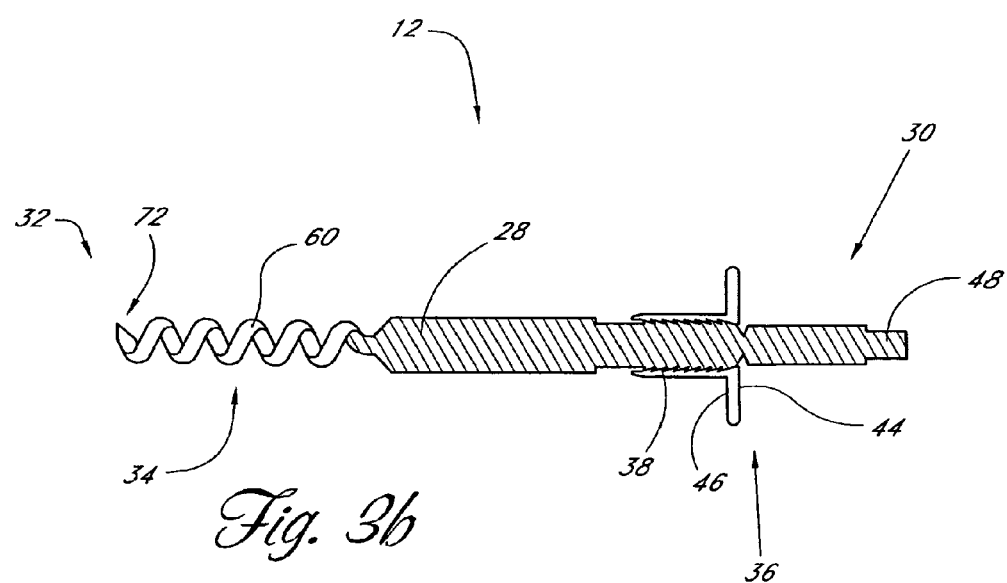
FIG. 3B is a side elevational cross section of a fixation device similar to that of FIG. 2.

In the illustrated embodiment, the bone contacting surface 46 of the flange 44 resides in or approximately on a plane which is inclined with respect to the longitudinal axis of the body 28. Any of a variety of angular relationships between the bone contacting surface 46 of the flange 44 and the longitudinal axis of the body 28 and housing 38 may be utilized, depending upon the anticipated entrance angle of the body 28 and associated entrance point surface of the femur 10. In general, the longitudinal axis extending through the head 14 and neck 16 of the human femur is inclined at an angle of approximately 126° from the longitudinal axis of the long body 17 of the femur 10. Angles between the longitudinal axis of body 28 and tissue contacting surface 46 within the range of from about 90° to about 140° will generally be utilized, often within the range of from about 100° to about 120°, for fixed angle fixation devices. Perpendicular flanges (i.e., 90°) are illustrated in FIGS. 3A and 3B.

The clinician can be provided an array of proximal anchors 36 of varying angular relationships between the bone contacting surface 46 and the longitudinal axis of the body 28 and housing 38 (e.g., 90°, 100°, 110°, 120°, and 130°). A single body 28 can be associated with the array such as in a single sterile package. The clinician upon identifying the entrance angle of the body 28 and the associated entrance point surface orientation of the femur 10 can choose the anchor 36 from the array with the best fit angular relationship, for use with the body 28.

Figure 9:
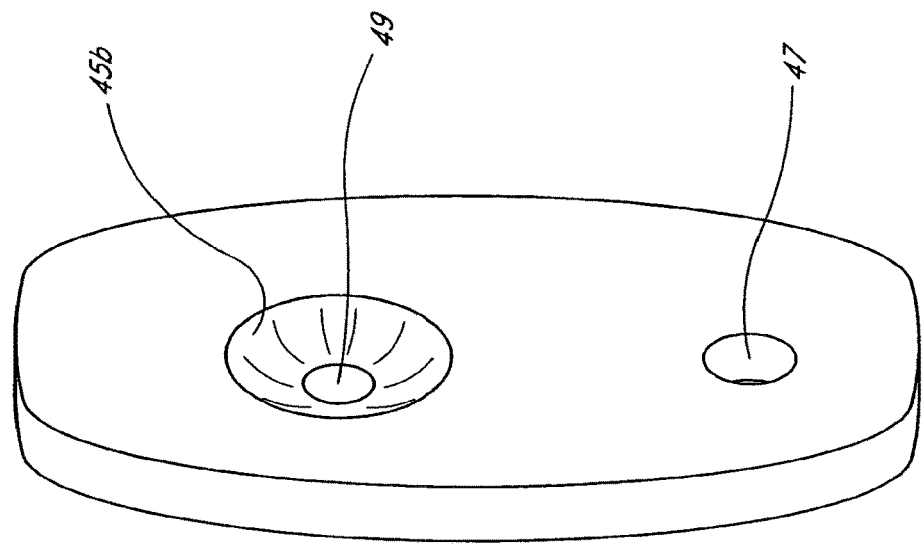
FIG. 9 is a front perspective view of the proximal anchor plate of FIG. 8.
Figure 8:
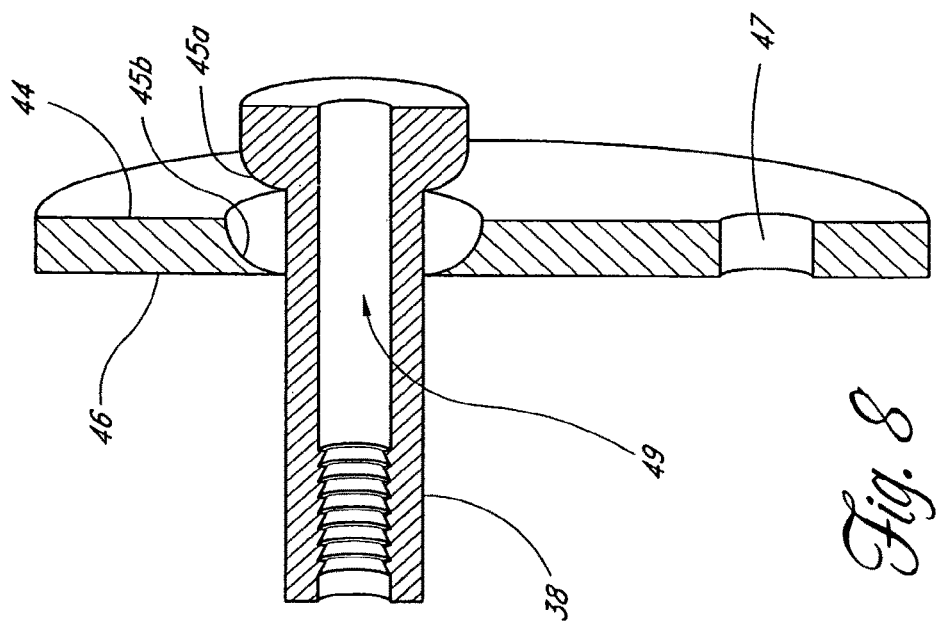
FIG. 8 is a cross sectional view through an angularly adjustable proximal anchor plate.

In accordance with an optional feature, illustrated in FIGS. 8 and 9, the flange 44 is angularly adjustable with respect to the longitudinal axis of the body 28. More specifically, in this embodiment, the tubular housing 38 is a separate component from the flange 44. The housing 38 and the flange 44 preferably include corresponding semi-spherical or radiused surfaces 45a, and 45b. The surface 45b surrounds an aperture 49 in the flange 44. This arrangement allows the housing 38 to extend through and pivot with respect to the flange 44. As such, the angular relationship between the bone contacting surface 46 of the flange 44 and the longitudinal axis of the body 28 can vary in response to the entrance angle.

As an independent feature in FIGS. 8 and 9, the flange 44 is enlarged and includes one or two or more openings 47 for receiving one or two or more femoral shaft screws (not shown). The flange 44 may be elongated anatomically distally parallel to the axis of the femur, so that it functions simultaneously as a plate, as will be discussed in connection with FIG. 6.

With reference back to FIGS. 3a and 3b, the proximal end 30 of the body 28 is preferably additionally provided with rotational coupling 48, for allowing the body 28 to be rotationally coupled to a driving device. Any of a variety of driving devices may be utilized, such as electric drills or hand tools which allow the clinician to manually rotate the cancellous bone anchor 34 into the head of the femur. Thus, the rotational coupling 48 may have any of a variety of cross sectional configurations, such as one or more flats or splines.

In one embodiment, the rotational coupling 48 comprises a proximal projection of the body 28 having a polygonal cross section, such as a hexagonal cross section. The rotational coupling 48 is illustrated as a male component, machined or milled or attached to the proximal end 30 of the body 28. However, the rotational coupling may also be in the form of a female element, such as a hexagonal or other noncircular cross sectioned lumen extending throughout a proximal portion or the entire length of the body 28. Although illustrated as solid throughout, the body 28 may be cannulated to accommodate installation over a placement wire as is understood in the art. The cross section of the central cannulation can be made non circular, e.g., hexagonal, to accommodate a corresponding male tool for installation or removal of the device regardless of the location of the proximal break point, as will be discussed.

The body 28 may be provided with at least one and preferably two or three or more break points 50 spaced axially apart along the proximal portion of the body 28. Break points 50 comprise a weakened transverse plane through the body 28, which facilitate severing of the proximal portion of the body 28 following proper tensioning of the proximal anchor 36. Break point 50 may be constructed in any of a variety of ways, such as by machining or milling an annular recess into the exterior wall of the body 28, or created one or more transverse perforations through the body 28 such as by mechanical, laser, or EDM drilling.

The body 28 may also be provided with at least one and preferably two or three or more graduation markings axially spaced along the proximal portion of the body 28. Such graduation markings can be used to indicate how far the body 28 has been inserted into the bone. Such graduation markings may include indicia indicating the distance (e.g., in millimeters or inches) from the proximal surface of the bone to the distal tip of the distal bone anchor 34.

In all of the embodiments illustrated herein, the distal anchor 34 comprises a helical locking structure 60 for engaging cancellous and/or distal cortical bone. In the illustrated embodiment, the locking structure 60 comprises a flange that is be wrapped around a central core 62 or an axial lumen, as discussed below. The central core 62 or axial lumen defines a minor diameter of the helical locking structure 60. In a similar manner, the outer edge of the helical flange 60 defines a major diameter or outer boundary of the helical locking structure 60. The flange extends through at least one and generally from about two to about 50 or more full revolutions depending upon the axial length of the distal anchor and intended application. For most femoral neck fixation devices, the flange will generally complete from about 2 to about 20 revolutions. The helical flange 60 is preferably provided with a pitch and an axial spacing to optimize the retention force within cancellous bone, to optimize compression of the fracture.

The helical flange 60 of the embodiment illustrated in FIG. 1 is shaped generally like a flat blade or radially extended screw thread. However, it should be appreciated that the helical flange 60 can have any of a variety of cross sectional shapes, such as rectangular, triangular or other as deemed desirable for a particular application through routine experimentation in view of the disclosure herein. The ratio of the major diameter to the minor diameter can be optimized with respect to the desired retention force within the cancellous bone and giving due consideration to the structural integrity and strength of the distal anchor 34. Another aspect of the distal anchor 34 that can be optimized is the shape of the major and minor diameters, which in the illustrated embodiment are generally cylindrical with a tapered distal end 32.

The distal end 32 and/or the outer edges of the helical flange 60 may be atraumatic (e.g., blunt or soft). This inhibits the tendency of the fixation device 12 to migrate anatomically proximally towards the hip joint bearing surface after implantation (i.e., femoral head cut-out). Distal migration is also inhibited by the dimensions and presence of the proximal anchor 36, which has a larger footprint than conventional screws.

Figure 2:
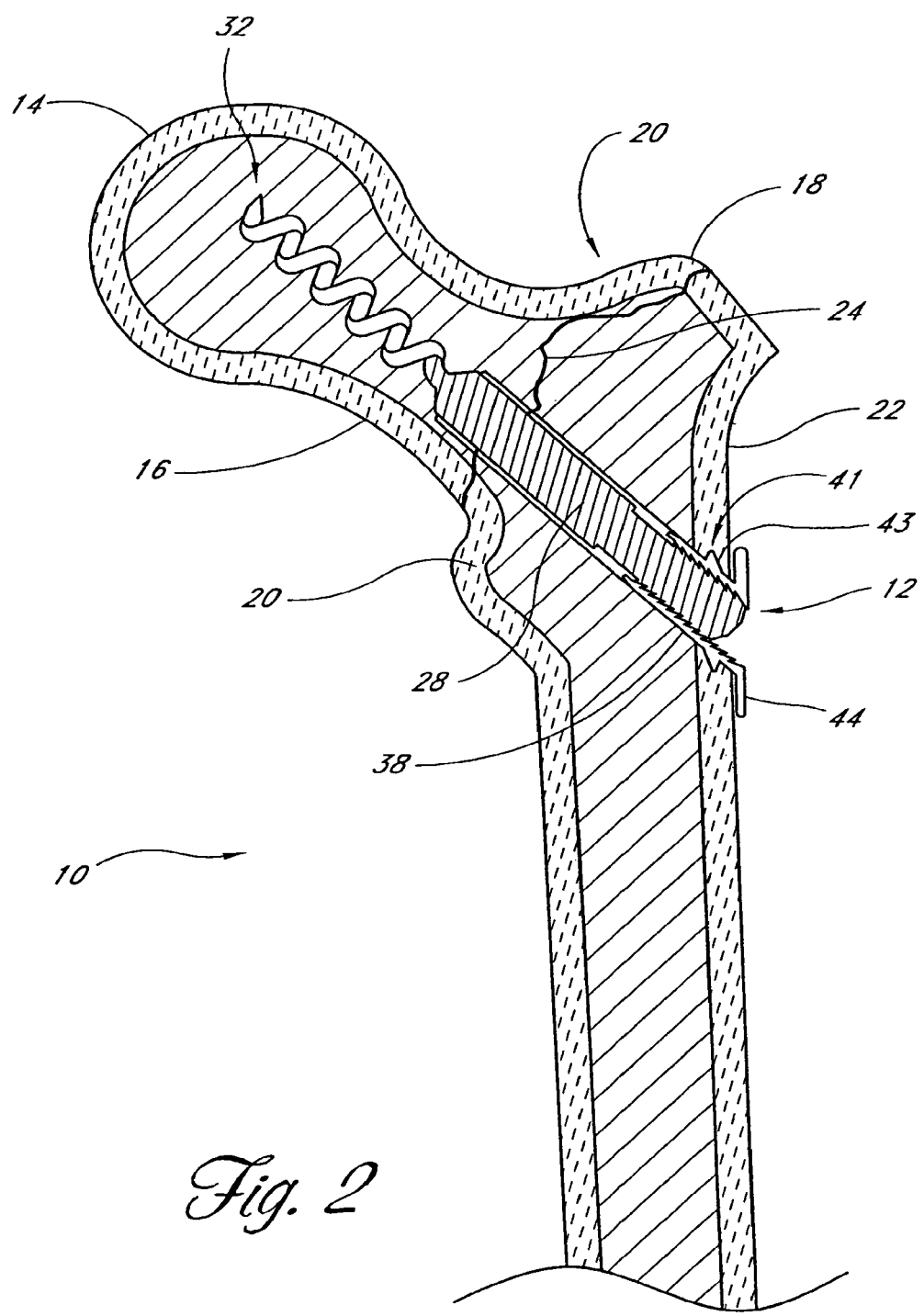
FIG. 2 is a posterior cross section as in FIG. 1, with a modified fixation device positioned therein.

Referring to FIGS. 2 and 3B, a variation of the distal anchor 34 is illustrated. The distal anchor 34 comprises an elongated helical locking structure 60 that is spirally wrapped about an axial lumen through at least one and preferably from about two to about 20 or more full revolutions. The axial lumen defines a minor diameter that is generally cylindrical. As with the previous embodiment, the elongated body 60 is provided with a pitch and an axial spacing to optimize the retention force within cancellous bone, which optimizes compression of the fracture. The tip 72 of the elongated body 60 may be pointed. Although not illustrated, this variation is particularly suited for a canulated fixation device 12. That is, a design wherein a central lumen extends through the body 28 and the distal anchor 34.

Figure 5:
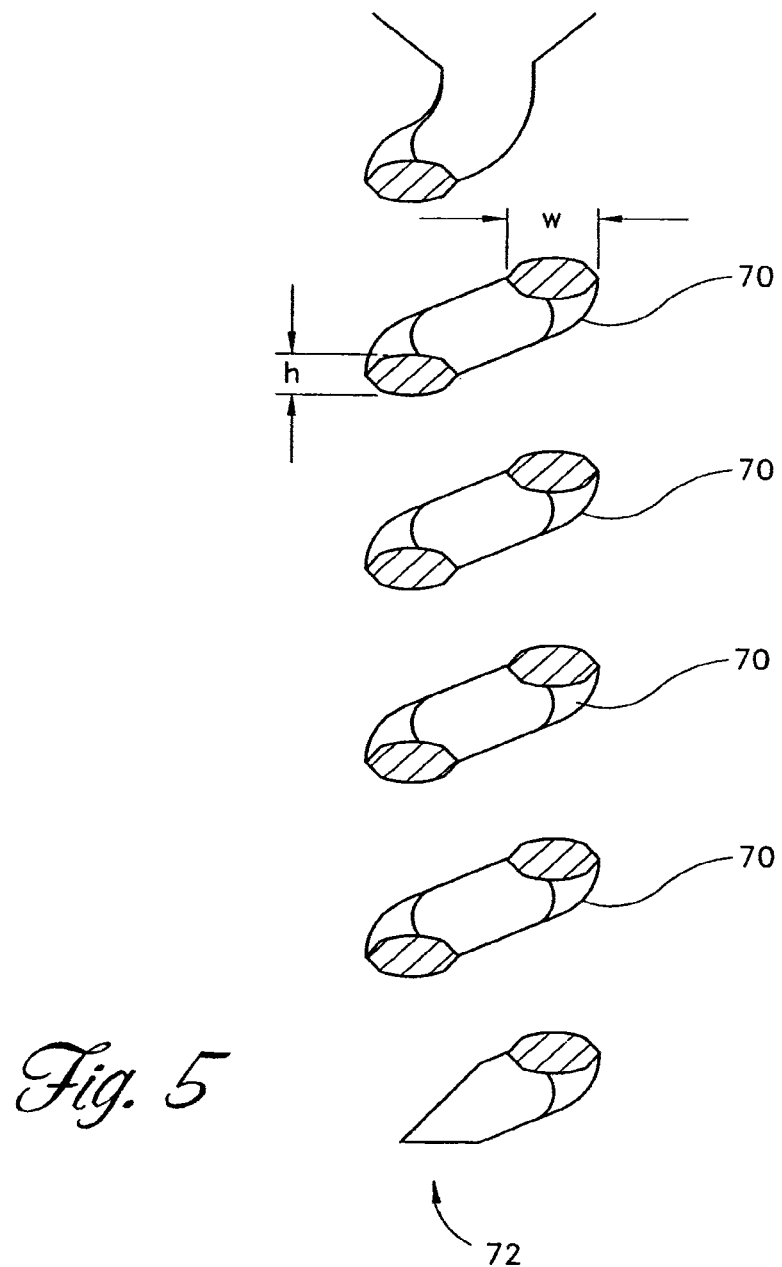
FIG. 5 is an axial cross sectional view through a distal end of a fixation device of the present invention.

FIG. 5 is an axial cross sectional view through a distal anchor of the type illustrated in FIGS. 2 and 3B. FIG. 5 also illustrates the cross-section of the helical flange which forms the spiral locking structure. The cross-section has a width w, and a height h. Through routine experimentation, the shape, the width w and height h of the elongated body can be varied to optimize the retention force within cancellous bone. When w is approximately equal to h, the cross section can be circular, square or faceted. In general, w and h are within the range of from about 1 mm to about 8 mm for use in the femoral neck application.

With reference to FIG. 3C, another variation of the distal anchor 34 is illustrated. In this arrangement, the distal anchor 34 forms a double helix comprising two elongated structures 360, 362 spirally wrapped around an axial lumen through at least one and preferably from about 2 to about 20 or more full revolutions. As with the previous embodiments, the shape, the width w and height h of the elongated bodies 360, 362 along with pitch and an axial spacing can be optimized through routine experimentation to optimize the retention force within cancellous bone, which optimizes compression of the fracture. The diameter of the axial lumen can also be optimized. The tip 364 of helical flanges 360, 362 may be tapered or pointed to permit easier insertion through self-tapping and self-drilling. The double helix design may be incorporated into any of the designs disclosed elsewhere herein. In one embodiment for use in the femoral neck, the elongated structures 360, 362 have a generally rectangular cross sectional shape with a height and width within the range of about 1.0-4.0 millimeters. In such an embodiment, the major diameter is in the range of about 4.0-15 millimeters, the minor diameter is in the range of about 2.0-8.0 millimeters, and the pitch is in the range of from about 3 to about 12 threads per inch.

With reference to FIG. 3D, yet another variation of the distal anchor 34 is illustrated. In this embodiment, the anchor 34 comprises a helical flange 370 having a generally "V" shaped cross-section. The illustrated flange 370 has sides angled at about 60-degrees, forming two load bearing surfaces 372, 374 and a blunted outer edge 376. The proximally facing surface 372 carries the axial load to resist pullout. In this embodiment of the helical flange 370, the minor diameter is approximately equal to zero. Such an arrangement advantageously leaves more bone in place when the distal anchor 34 is inserted into the distal bone fragment such as a portion of the femur 10. However, it should be appreciated that in a modified arrangement the minor diameter can be increased giving due consideration to the balance between the desired retention force within the cancellous bone and the structural integrity and strength of the distal anchor 34. The angle between the two surfaces 372, 374 along with the pitch and axial spacing of the helical flange 370 are selected to optimize the retention force within cancellous bone, to optimize compression of the fracture.

Still yet another variation of the distal anchor 34 is illustrated in FIG. 3E. In this variation, the distal anchor 34 comprises a helical flange 380 having a buttress thread design. That is, the flange 380 has a generally rectangular cross-section, and extends radially outwardly and in some embodiments is inclined proximally to form a proximally concave spiral. This arrangement enhances the pullout strength of the distal anchor 34 because the bearing surfaces 382, 384 of the flange 380 lie generally perpendicular to the load direction. As with the previous arrangement, the helical flange 380 has a minor diameter that is approximately equal to zero. However, it should be appreciated that in a modified arrangement the minor diameter can be increased minor diameter can increased giving due consideration to the balance between the desired retention force within the cancellous bone and the structural integrity and strength of the distal anchor 34. As with the previous embodiments, the pitch and axial spacing can also be optimized to enhance the retention force within cancellous bone and to optimize compression across the fracture.

Referring to FIGS. 3F and 3G, additional variations of distal anchor 34 are illustrated. With initial reference to FIG. 3F, the distal anchor 34 comprises at least three helical threads or flanges 390, 392, 394 spirally wrapped around a generally cylindrical central core 395, which in the illustrated arrangement also defines the wall of an axial lumen 397 that can extend through the body 28. The major diameter of the distal anchor 34 is generally cylindrical. The leading tips 396 of the helical flanges 390, 392, 394 may be sharpened so as to aid the screw in being self tapping and/or self drilling. In this arrangement, the helical flanges 390, 392, 394 can be provided with a lower pitch as compared to the arrangement described above. Moreover, as compared to the previous arrangements, this arrangement requires less turns to insert the distal anchor 34 any given axial distance.

For example, in an embodiment for use in the femoral neck, the pitch of the helical flanges 390, 392, 394 may be within the range of from about 2 to about 12 threads per inch. The distal anchor 34 therefore requires fewer turns during insertion to achieve the same axial travel as a single helix thread having a greater pitch. In addition, this arrangement leaves more of the bone intact. In a modified arrangement, the distal anchor can include two or four helical flanges such as flanges 390, 392, 394. The number, pitch and axial spacing of the helical flanges can be optimized through routine experimentation in light of the disclosure herein. In one dual helical flange embodiment, the minor diameter is about 4.5 millimeters, the major diameter is about 7.0 millimeters and the pitch is about 5.5 threads per inch.

In FIG. 3G, the distal anchor 34 comprises split triple helix distal anchor design that is similar to the arrangement described above. However, in this arrangement, one of the helical flanges is cut through to the axial lumen 397 that is defined by the central core 395. As such, three flanges 400, 402, 403 remain wrapped around the central core 395. As compared to the previous arrangement, this arrangement leaves more bone intact. As with the previous embodiments, the pitch and axial spacing can be optimized through routine experimentation. A split double helix, with two flanges or threads may also be provided.

FIGS. 3H and 3I illustrate more variations of the distal anchor 34. In FIG. 3H, the distal anchor 34 comprises a generally V-shaped flange 410 that is wrapped around a central core 412 that also defines a central lumen 413, which can extend through the body 28. The major diameter of the V-shaped flange 410 is generally cylindrical. In contrast, the minor diameter of the central core tapers in the distal direction. As such, in the illustrated arrangement, the central core disappears into the generally cylindrical central lumen 413 at a point in between the proximal and distal ends of the threads, and, in the illustrated embodiment, at approximately the longitudinal center 414 of the distal anchor 34. This arrangement strengthens the proximal portion 416 of the distal anchor 34, where stretching and fatigue may be most likely to occur on pullout. It is anticipated that the shape of the flange 410 along with the pitch, axial spacing and the taper of the central core can be optimized through routine experimentation given the disclosure herein.

In FIG. 3I, the distal anchor 34 also comprises a V-shaped helical flange 420 that is wrapped around an axial lumen. In this arrangement, both the major and minor diameters taper from the proximal end 422 of the anchor 34 to the distal end 424. At the distal end 424, the minor diameter is approximately equal to zero. In this arrangement, the distal end 424 of tapered distal anchor 34 can provide for self tapping while the proximal end 422 of the anchor 34 provides for self drilling. As with the previous embodiments, the shape, pitch, axial spacing of the helical flange 430 and the taper of the major and minor diameters can be further optimized through routine experimentation. In a modified arrangement, the helical flange 430 can be wrapped around a central core that tapers from the proximal end 422 to the distal end 424.

In any of the embodiments herein, an anti-rotation lock may be provided between the distal anchor and the proximal collar or plate, such as a spline or other interfit structure to prevent relative rotation of the proximal and distal ends of the device following implantation.

In use, the clinician first identifies a patient having a fracture to be treated, such as a femoral neck fracture, which is fixable by an internal fixation device. The clinician accesses the proximal femur, reduces the fracture if necessary and selects a bone drill and drills a hole 80 in accordance with conventional techniques. In the example of a femoral neck fracture, three holes and fixation devices will often be used as has been discussed. Preferably, the hole 80 has a diameter within the range from about 3 mm to about 8 mm. This diameter may be slightly larger than the diameter of the distal anchor 34. The hole 80 preferably extends up to or slightly beyond the fracture 24.

A fixation device 12 having an axial length and outside diameter suitable for the hole 80 is selected. The distal end 32 of the fixation device 12 is advanced distally into the hole 80 until the distal anchor 34 reaches the distal end of the hole 80. The proximal anchor 36 may be carried by the fixation device 12 prior to advancing the body 28 into the hole 80, or may be attached following placement of the body 28 within the hole 80. Once the body 28 is in place, the clinician may use any of a variety of driving devices, such as electric drills or hand tools to rotate the cancellous bone anchor 34 into the head of the femur.

While proximal traction is applied to the proximal end 30 of body 28, such as by conventional hemostats, pliers or a calibrated loading device, the proximal anchor 36 is advanced distally until the anchor 36 fits snugly against the outer surface of the femur or tissue adjacent the femur. Appropriate compression of the fixation device 12 across the fracture is accomplished by tactile feedback or through the use of a calibration device for applying a predetermined load on the implantation device. One advantage of the structure of the present invention is the ability to adjust compression independently of the setting of the distal anchor 34.

Following appropriate tensioning of the proximal anchor 36, the proximal extension 30 of the body 28 is preferably cut off, snapped off, unscrewed or otherwise removed. Body 28 may be cut using conventional saws, cutters or bone forceps which are routinely available in the clinical setting. Alternatively, the fixation device can be selected such that it is sized to length upon tensioning, so that no proximal projection remains.

Following removal of the proximal end 30 of body 28, the access site may be closed and dressed in accordance with conventional wound closure techniques.

With reference to FIG. 2, in one arrangement, the proximal anchor 36 can include one or more barbs 41 extending radially outwardly from the tubular housing 28. The barbs 41 may be radially symmetrically distributed about the longitudinal axis of the tubular housing 38. Each barb 41 is provided with a transverse engagement surface 43, for anchoring the proximal anchor 36 in the bone. The transverse engagement surface 43 may lie on a plane which is transverse to the longitudinal axis of the tubular housing 38 or may be inclined with respect to the longitudinal axis of the tubular housing 38. In either arrangement, the transverse engagement surface 43 generally faces the bone contacting surface 46 of the flange 44. As such, the transverse engagement surface 43 inhibits proximal movement of the proximal anchor 36 with respect to the bone.

The barbs 41 allow the bone fixation device to capture "secondary compression" of the fracture. As explained above, the bone fixation device can be used to provide an initial compression across the fracture when the proximal anchor 36 is appropriately tensioned. However, as the patient applies weight or stress to the bone post procedure, the fracture typically undergoes secondary compression, which further compresses the fracture. During such secondary compression, the barbs 41 prevent proximal movement of the proximal anchor 36 with respect to the bone. The ratchet-type structures 40, 42 of the proximal anchor 36 and the body 28 allow the proximal anchor 36 to move distally along the body 28. Thus, any slack caused by the secondary compression is taken up by the proximal anchor 36 as the retention structures 40, 42 prevent proximal movement of the proximal anchor 36 with respect to the body 29. This device is therefore self tightening after it has been implanted in the patient.

Preferably, the clinician will have access to an array of fixation devices 12, having, for example, different diameters, axial lengths and angular relationships. These may be packaged one per package in sterile envelopes or peelable pouches, or in dispensing cartridges which may each hold a plurality of devices 12. Upon encountering a fracture for which the use of a fixation device is deemed appropriate, the clinician will assess the dimensions and load requirements, and select a fixation device from the array which meets the desired specifications.

In some types of fractures such as a femoral neck fracture, a clinician may want to introduce two or three or more fixation devices 12 into the femoral head 14 to secure the fracture 24. This may be desirable if the clinician determines that, based upon the nature of the fracture 24, there is a possibility that the head 14 of the femur 10 could rotate about a single fixation device 12. Even minor rotation can inhibit the healing of the fracture. Significant rotation can result in failure of the fixation device or necrosis of the femoral head. Two fixation devices 12 may also be desirable where the direction of the fracture is generally parallel to the axis of implantation as is understood in the art.

Figure 6:
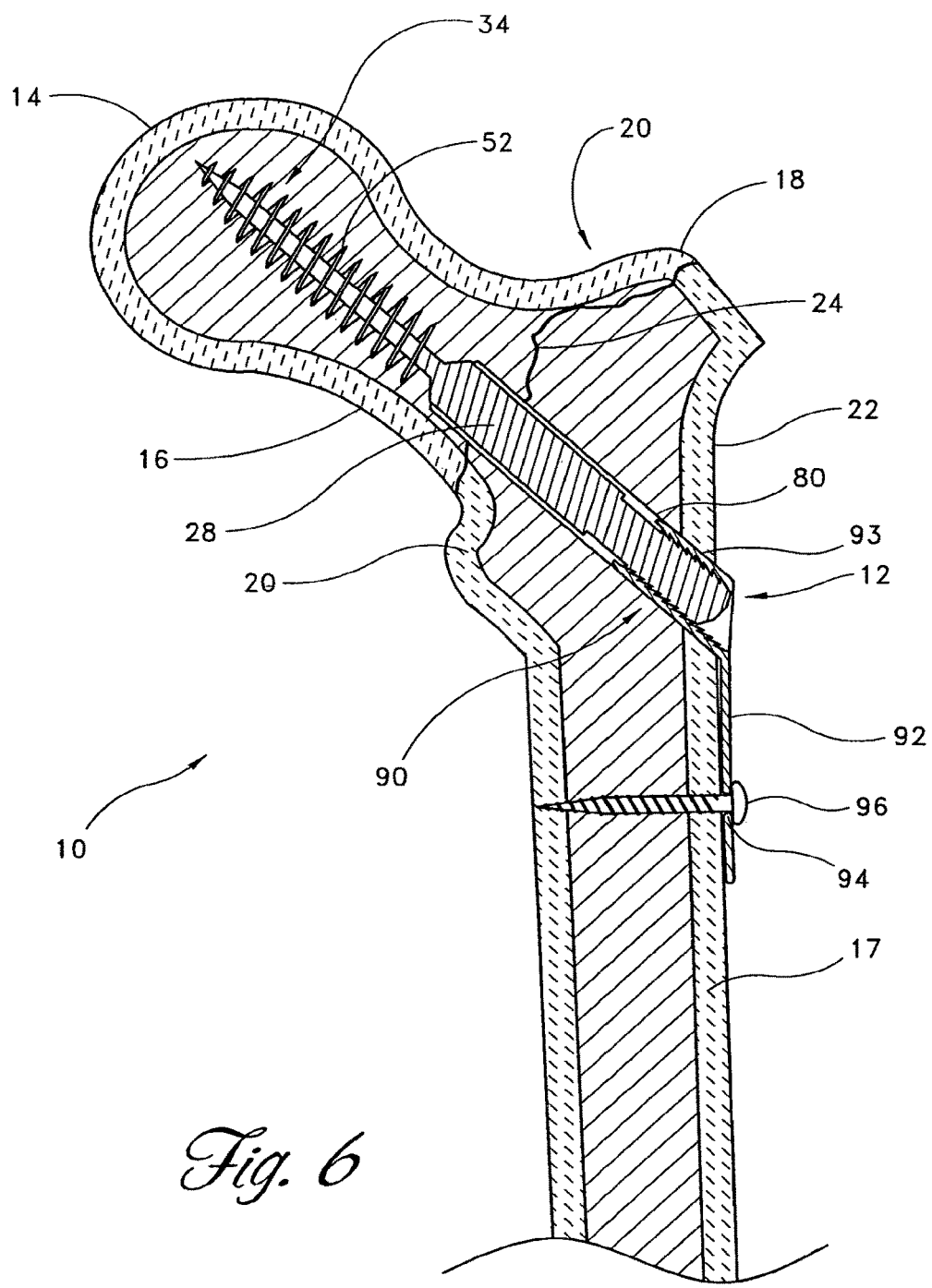
FIG. 6 is a posterior cross section as in FIG. 1, with a fixation device and integral proximal plate anchor positioned therein.

Referring to FIG. 6, there is disclosed a variation of the proximal anchor 36 in which the proximal anchor 36 is integrally formed with or attached to a plate. The fixation device 12 in FIG. 6 may otherwise be identical to the embodiments previously discussed. The proximal anchor 90 comprises an elongated flange 92, which extends from the housing 93 longitudinally down (anatomically caudad or distally) the body 17 of the femur 10. The elongated flange 92 preferably includes one or more openings 94 for receiving one or more femoral shaft screws 96. The flange 92 may or may not extend above (anatomically proximal to) the housing 93. Elimination of a proximal flange may more easily permit rotational removal of the proximal anchor 36 from the body 28 by reverse rotation in an inclined flange embodiment.

Figure 6A:
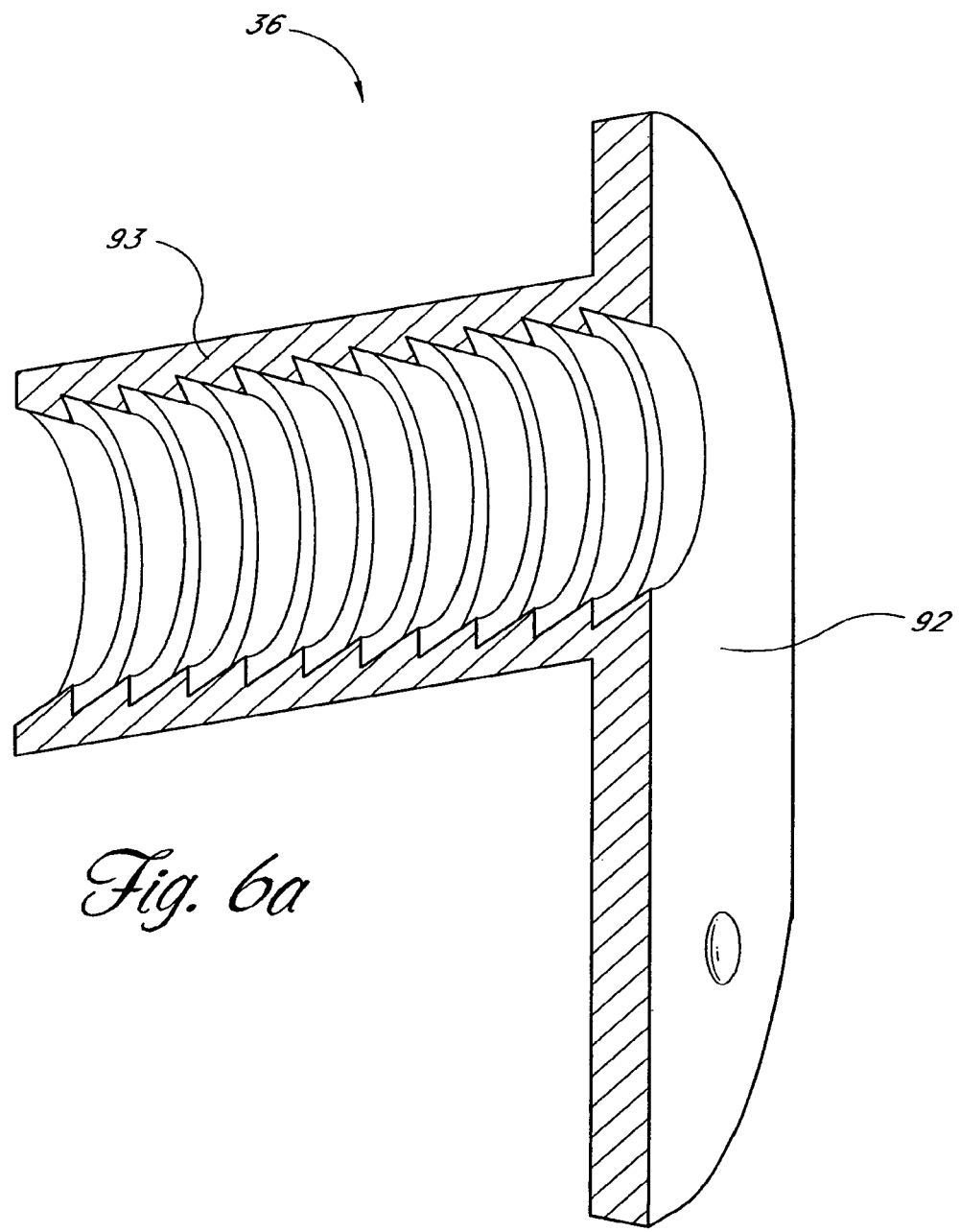
FIG. 6A is a cross sectional schematic view of a combination proximal anchor and plate in accordance with the present invention.

Referring to FIG. 6A, there is illustrated a cross sectional schematic view of an integral proximal anchor 36 and proximal plate. The dimensions and orientation of the proximal anchor 36 may be varied widely, depending upon the intended application. For example, a longitudinal axis of the housing 93 may be inclined or perpendicular with respect to the plane of flange 92. The flange 92 may have any of a variety of dimensions and profiles, depending upon the intended application. Lengths of the plate 92 in the vertical direction as illustrated on FIG. 6A, for use in femoral neck fixation fractures, may range from at least about 0.5 inches to about 10 inches or more. The plate 92 may be planar as illustrated, particularly in small plate embodiments, or may be curved or contoured to improve seating of the plate 92 against the adjacent bone. Plate 92 may be provided with one or more apertures for receiving bone screws or other fixation devices as illustrated in FIGS. 6 and 7A.

Figure 7A:
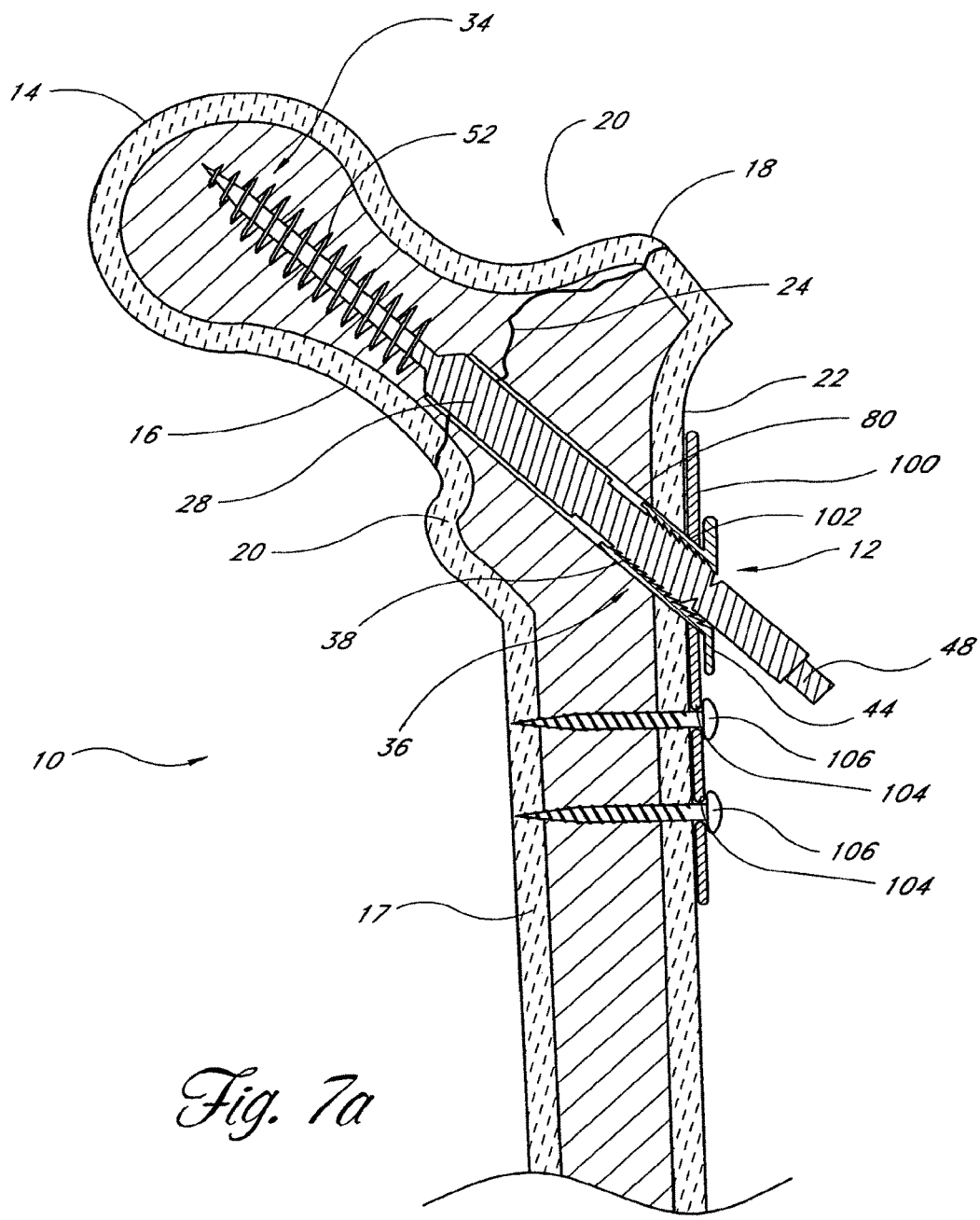
FIG. 7A is a posterior cross section as in FIG. 1, with a plate and fixation device positioned therein.

Referring to FIG. 7A, the fixation device 12 is schematically illustrated in combination with a conventional plate 100. The fixation device 12 in FIG. 7A may be identical to the embodiments described elsewhere herein. The fixation device 12 is used with an elongated side support or plate 100, which extends longitudinally above and below the hole 80. The elongated side plate 100 includes an opening 102 that preferably has a diameter that is slightly larger than the diameter of the housing 38. The elongated side plate 100 preferably also includes one or more openings 104 for receiving one or more femoral shaft screws 106. Advantageously, the elongated side plate 100 spreads the forces exerted by the flange 44 across a larger area of the femur 17, and affects the distribution of load. In an alternate embodiment, the elongated side plate can 100 include one or more openings above the housing 38 for receiving trochanteric anchor screws (not shown).

Figure 7B:
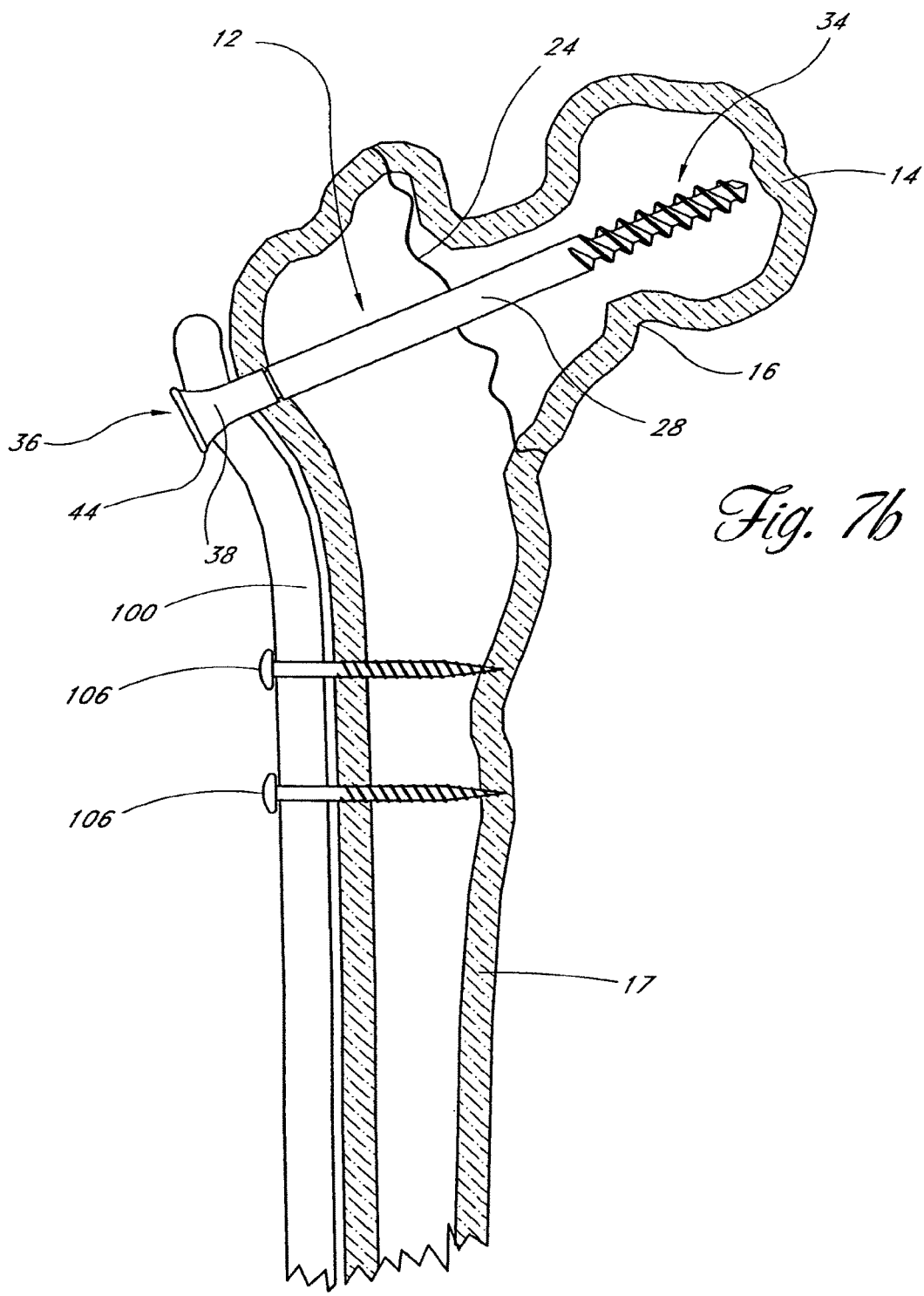
FIG. 7B is a cross section through a proximal portion of the femur, illustrating the use of a fixation device in combination with a plate.

A contoured side plate 100 is illustrated in FIG. 7B. The proximal anchor 36 is also formed with a tapered (e.g. conical or concave outwardly) bone or plate contacting surface on flange 44.

Figure 7C:
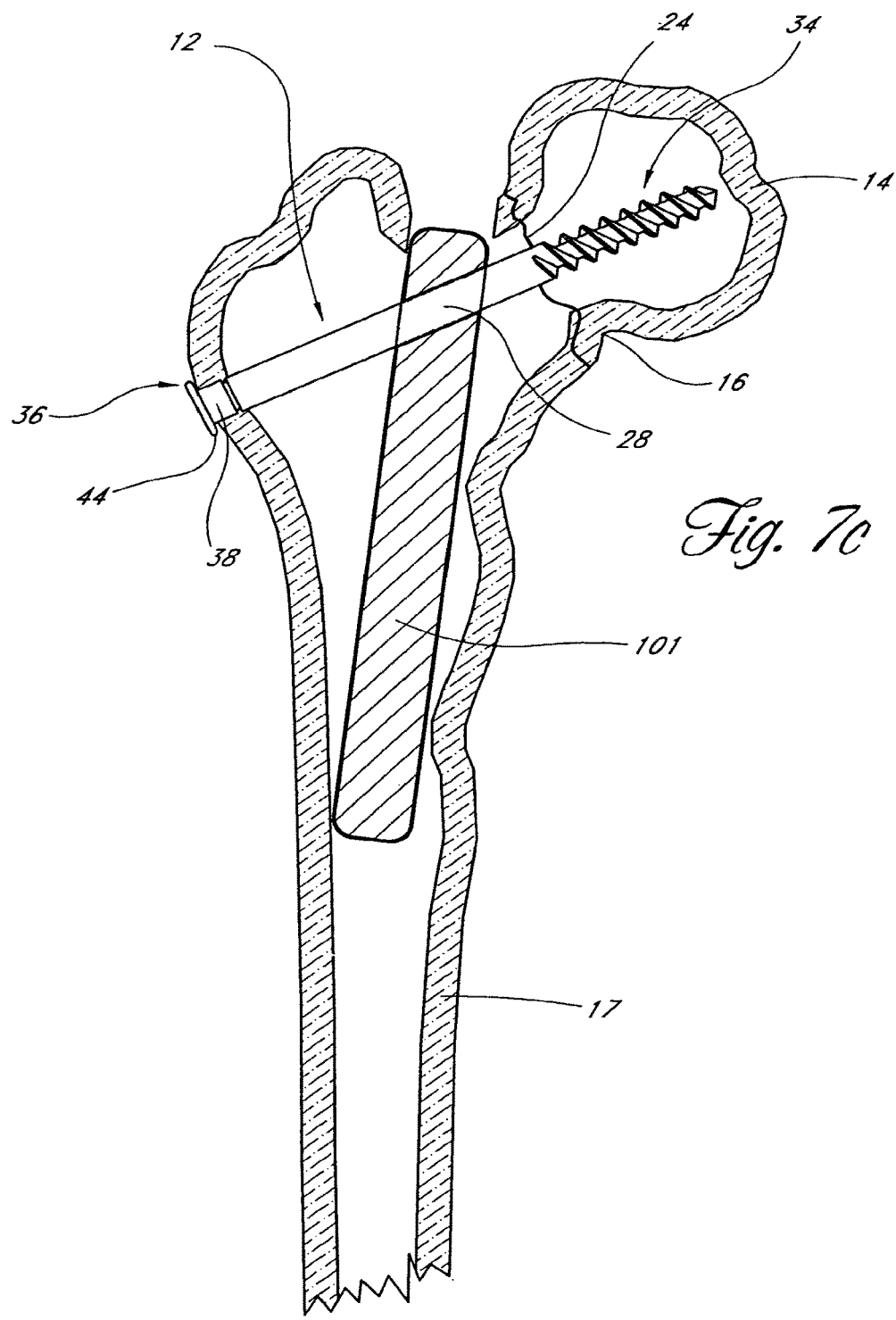
FIG. 7C is a cross section as in FIG. 7B, illustrating the use of a fixation device of the present invention in combination with an intramedullary nail.

The fixation device 12 of the present invention may also be used in combination with intramedullary nails or rods 101 as schematically illustrated in FIG. 7C, as will be understood by those of skill in the art.

Figure 10:
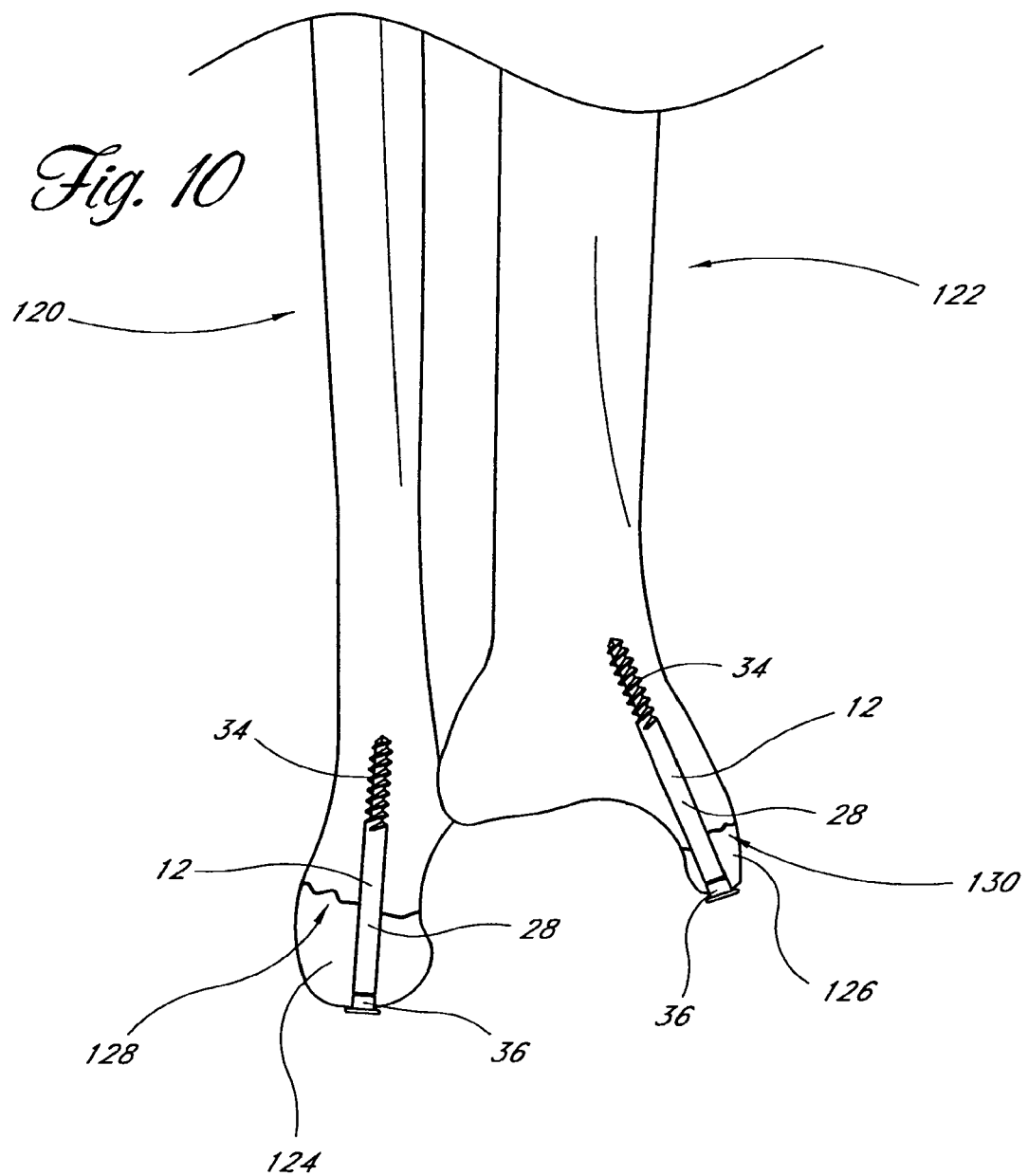
FIG. 10 is an anterior view of the distal tibia and fibula, with fixation devices across lateral and medial malleolar fractures.

The fixation device 12 of the present invention may be used in any of a wide variety of anatomical settings beside the proximal femur, as has been discussed. For example, lateral and medial malleolar fractures can be readily fixed using the device of the present invention. Referring to FIG. 10, there is illustrated an anterior view of the distal fibula 120 and tibia 122. The fibula 120 terminates distally in the lateral malleolus 124, and the tibia 122 terminates distally in the medial malleolus 126.

A fixation device 12 in accordance with the present invention is illustrated as extending through the lateral malleolus 124 across the lateral malleolar fracture 128 and into the fibula 120. Fixation device 12 includes a distal anchor 34 for fixation within the fibula 120, an elongate body 28 and a proximal anchor 36 as has been discussed.

FIG. 10 also illustrates a fixation device 12 extending through the medial malleolus 126, across a medial malleolar fracture 130, and into the tibia 122. Although FIG. 10 illustrates fixation of both a lateral malleolar fracture 128 and medial malleolar fracture 130, either fracture can occur without the other as is well understood in the art. Installation of the fixation devices across malleolar fractures is accomplished utilizing the same basic steps discussed above in connection with the fixation of femoral neck fractures.

The fixation devices of the present invention may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful:

(1) the blend of poly(p-dioxanone) and a lactide/glycolide copolymer, as disclosed in U.S. Pat. No. 4,646,741 which is incorporated by reference.

(2) the glycolide-rich blend of two or more polymers, one polymer being a high lactide content polymer, and the other being a high glycolide content disclosed in U.S. Pat. No. 4,889,119 which is incorporated by reference.

Additional bioabsorbable materials are disclosed in copending application Ser. No. 09/558,057 filed Apr. 26, 2000, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate in a bioabsorbable construction. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A fusion device, comprising:
an elongate body having a proximal end and a distal end;
a cancellous bone anchor on the distal end, the cancellous bone anchor comprising a helical member wrapped about a respective central axis, an outer edge of the helical member defining an outer boundary;
a break point on the proximal end;
a proximal anchor axially movably carried on the body; and
a first surface structure on an external surface of the body that cooperates with a complementary second surface structure on the proximal anchor, wherein the first and second surface structures permit advancing the proximal anchor along a span of the body in the distal direction but that resist axial proximal movement of the proximal anchor at all positions along the span of the body; wherein the proximal anchor comprises an outwardly extending flange and a tubular member extending longitudinally away from the flange towards the cancellous bone anchor, wherein an internal surface of the tubular member comprises the second surface structure.

2. The fusion device of claim 1, wherein the elongate body comprises two or more break points spaced axially apart along the proximal end.

3. The fusion device of claim 1, wherein the break point is proximal the proximal anchor following proper tensioning of the proximal anchor.

4. The fusion device of claim 1, wherein the proximal end extends proximally from the proximal anchor following proper tensioning of the proximal anchor.

5. The fusion device of claim 1, wherein the proximal end comprises a rotational coupling configured to allow the elongate body to be rotationally coupled to a driving device.

6. The fusion device of claim 1, wherein the elongate body comprises markings axially spaced along the proximal end.

7. The fusion device of claim 1, wherein the flange forms an angle with a longitudinal axis of the elongate body.

8. The fusion device of claim 7, wherein the angle is greater than 90°.

9. The fusion device of claim 7, wherein the angle is fixed.

10. The fusion device of claim 1, further comprising a plate having an opening configured to receive the fusion device.

11. The fusion device of claim 10, wherein the plate is contoured.

12. A fusion device, comprising:
an elongate body having a proximal end and a distal end;
a cancellous bone anchor on the distal end, the cancellous bone anchor comprising a helical member wrapped about a respective central axis an outer edge of the helical member defining an outer boundary;
a break point on the proximal end;
a unitary proximal anchor axially movably carried on the body; and
a first surface structure on an external surface of the body that cooperates with a complementary second surface structure on an internal surface of the unitary proximal anchor, wherein the first and second surface structures permit advancing the unitary proximal anchor along a span of the body in the distal direction but that resist axial proximal movement of the unitary proximal anchor at all positions along the span of the body; wherein the unitary proximal anchor comprises an outwardly extending flange and a tubular member extending longitudinally away from the flange towards the cancellous bone anchor.

13. The fusion device of claim 12, wherein the elongate body comprises two or more break points spaced axially apart along the proximal end.

14. The fusion device of claim 12, wherein the break point is proximal the unitary proximal anchor following proper tensioning of the unitary proximal anchor.

15. The fusion device of claim 12, wherein the proximal end extends proximally from the unitary proximal anchor following proper tensioning of the unitary proximal anchor.

16. The fusion device of claim 12, wherein the proximal end comprises a rotational coupling configured to allow the elongate body to be rotationally coupled to a driving device.

17. The fusion device of claim 12, wherein the elongate body comprises markings axially spaced along the proximal end.

18. The fusion device of claim 12, wherein the flange forms an angle with a longitudinal axis of the elongate body.

19. The fusion device of claim 18, wherein the angle is greater than 90°.

20. The fusion device of claim 18, wherein the angle is fixed.

* * * * *